United States Patent
Ganesh

(10) Patent No.: US 11,008,571 B2
(45) Date of Patent: May 18, 2021

(54) BETA CATENIN NUCLEIC ACID INHIBITOR MOLECULE

(71) Applicant: Dicerna Pharmaceuticals, Inc., Lexington, MA (US)

(72) Inventor: Shanthi Ganesh, Shrewsbury, MA (US)

(73) Assignee: Dicerna Pharmaceuticals, Inc., Lexington, MA (US)

(*) Notice: Subject to any disclaimer, the term of this patent is extended or adjusted under 35 U.S.C. 154(b) by 0 days.

(21) Appl. No.: 16/754,452

(22) PCT Filed: Oct. 17, 2018

(86) PCT No.: PCT/US2018/056317
§ 371 (c)(1),
(2) Date: Apr. 8, 2020

(87) PCT Pub. No.: WO2019/079472
PCT Pub. Date: Apr. 25, 2019

(65) Prior Publication Data
US 2020/0270606 A1    Aug. 27, 2020

Related U.S. Application Data

(60) Provisional application No. 62/573,999, filed on Oct. 18, 2017.

(51) Int. Cl.
| | | |
|---|---|---|
| *C12N 15/11* | (2006.01) | |
| *C12N 15/113* | (2010.01) | |
| *A61P 35/00* | (2006.01) | |
| *A61K 9/00* | (2006.01) | |
| *A61K 9/127* | (2006.01) | |
| *A61K 9/51* | (2006.01) | |

(52) U.S. Cl.
CPC .......... *C12N 15/113* (2013.01); *A61K 9/0019* (2013.01); *A61K 9/127* (2013.01); *A61K 9/51* (2013.01); *A61P 35/00* (2018.01); *C12N 2310/11* (2013.01); *C12N 2310/321* (2013.01); *C12N 2310/322* (2013.01)

(58) Field of Classification Search
CPC .................................................... C12N 15/113
See application file for complete search history.

(56) References Cited

U.S. PATENT DOCUMENTS

2011/0003881 A1    1/2011   Brown

FOREIGN PATENT DOCUMENTS

WO    2017/160983 A1    9/2017

OTHER PUBLICATIONS

International Search Report and Written Opinion dated Jan. 15, 2019 for International Application No. PCT/US2018/056317 (Authorized officer, Lee W. Young), 9 pages.
Ganesh et al., "Direct Pharmacological Inhibition of β-Catenin by RNA Interference in Tumors of Diverse Origin", Molecular Cancer Therapeutics, Sep. 2016, vol. 15, No. 9, pp. 2143-2154.

*Primary Examiner* — Ekaterina Poliakova-Georgantas
(74) *Attorney, Agent, or Firm* — Byron V. Olsen; MH2 Technology Law Group, LLP

(57) ABSTRACT

Provided herein is a potent, optimized β-catenin nucleic acid inhibitor molecule with a unique pattern of modified nucleotides. Also provided are methods and compositions for reducing β-catenin expression and methods and compositions for treating cancer.

18 Claims, 17 Drawing Sheets
Specification includes a Sequence Listing.

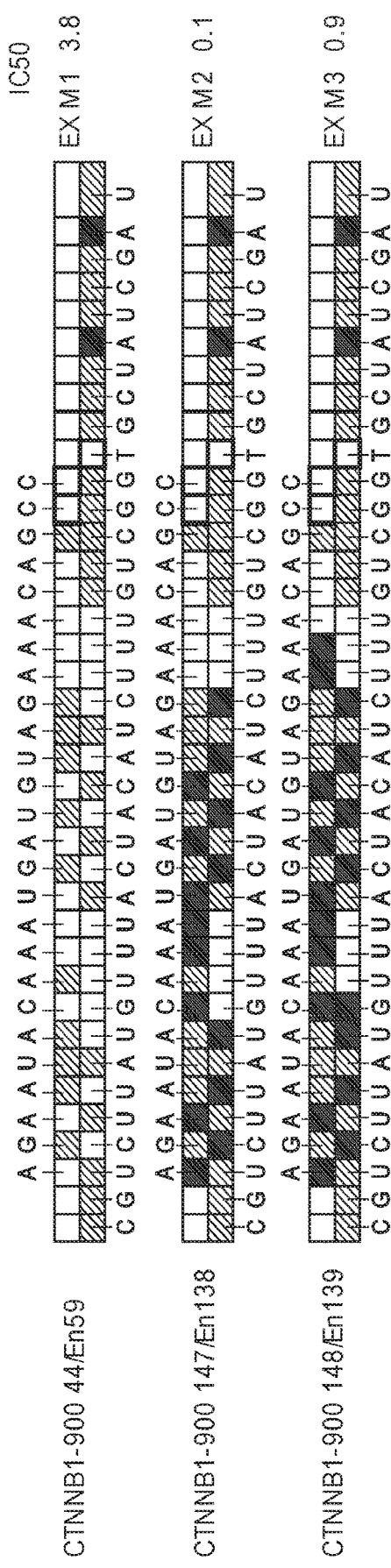
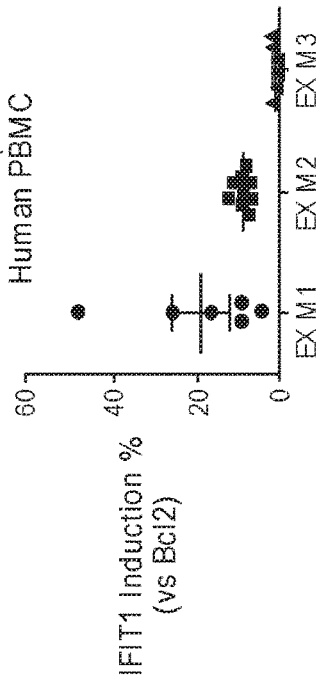
FIG. 2A
FIG. 2B

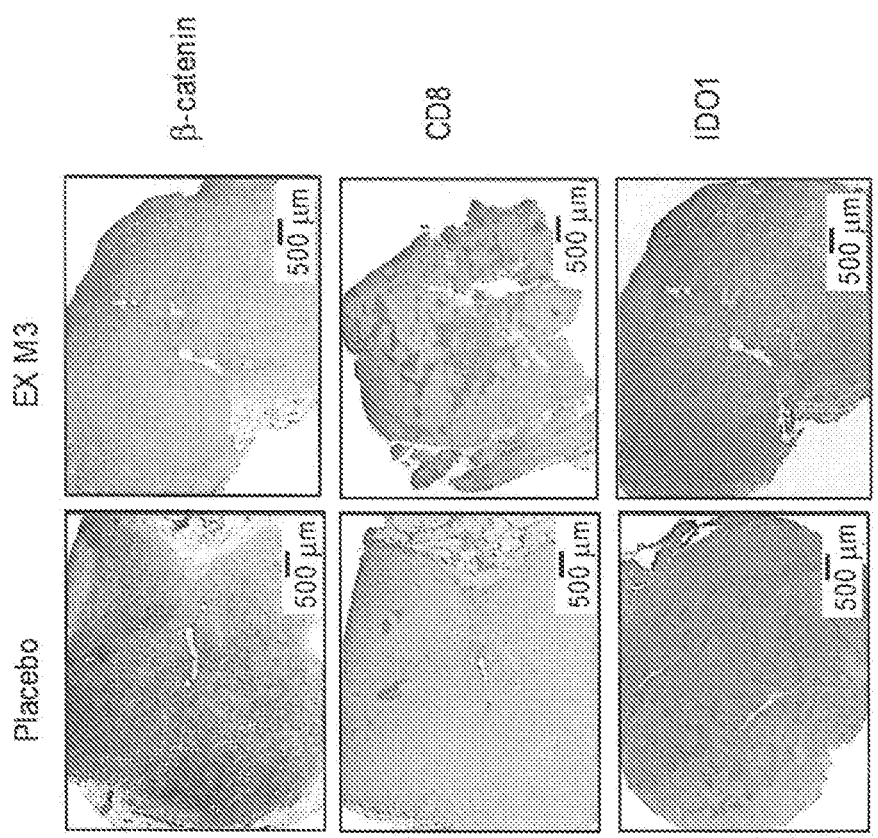
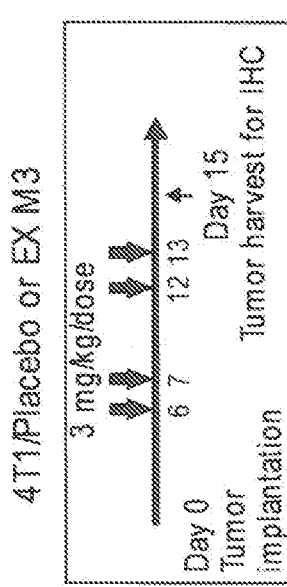
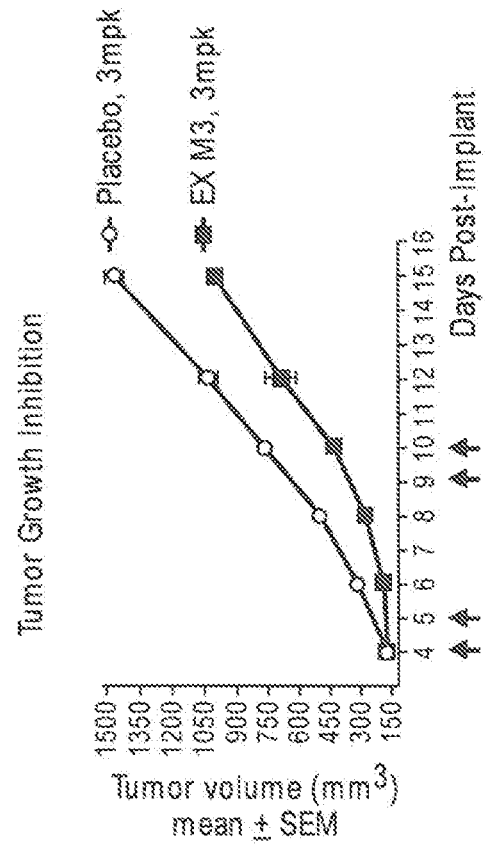
FIG. 7A
FIG. 7B
FIG. 7C

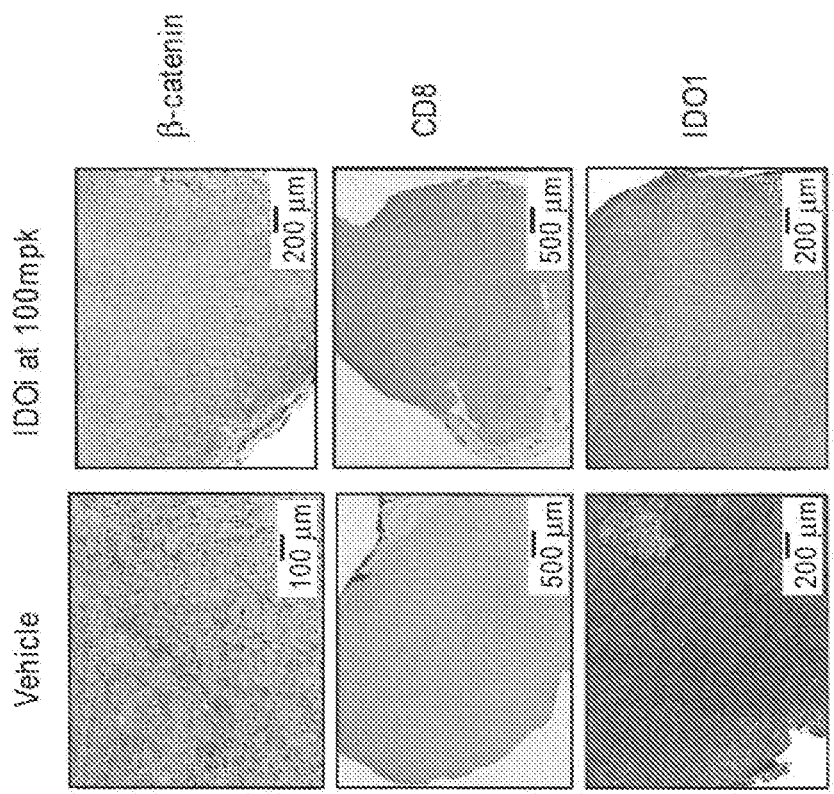
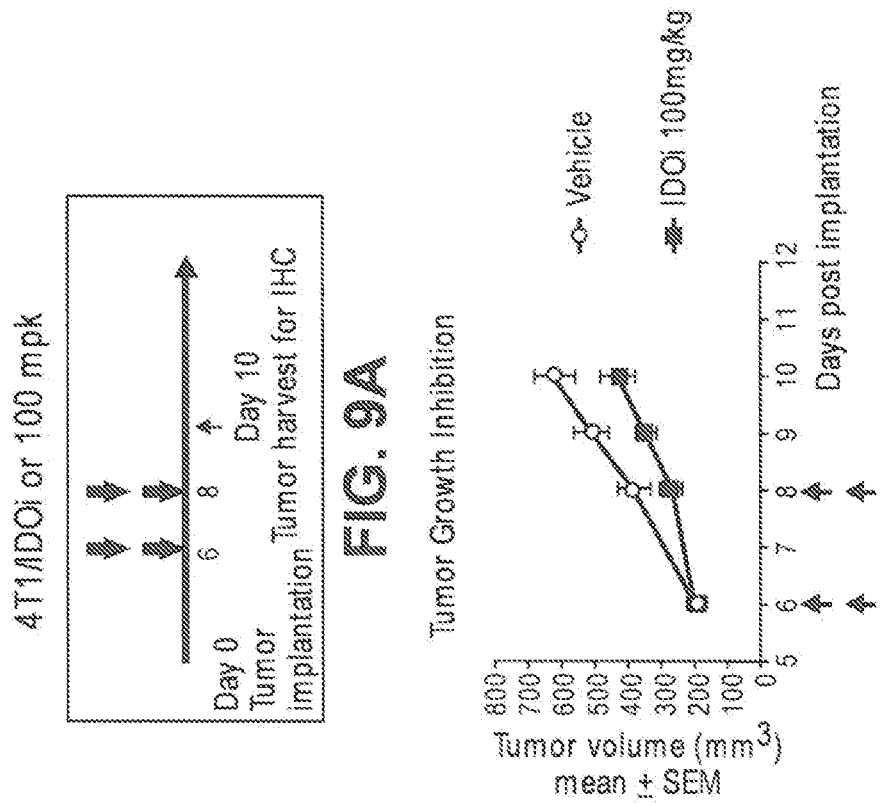
FIG. 9A
FIG. 9B
FIG. 9C

BETA CATENIN NUCLEIC ACID INHIBITOR MOLECULE

CROSS-REFERENCE TO RELATED APPLICATIONS

This application is a U.S. National Stage application of PCT/US2018/056317 filed 17 Oct. 2018, which claims priority to U.S. Provisional Patent Application No. 62/573,999, entitled "BETA CATENIN NUCLEIC ACID INHIBITOR MOLECULE," filed on Oct. 18, 2017, the entire contents of which are incorporated herein by reference in their entireties.

SEQUENCE LISTING

The instant application contains a Sequence Listing which has been filed electronically in ASCII format and is hereby incorporated by reference in its entirety. Said ASCII copy, created on Oct. 11, 2018, is named 0243_0008-PCT_SL.txt and is 19,219 bytes in size.

BACKGROUND

β-catenin, an oncogene, is a key mediator of Wnt signaling in cells. β-catenin serves several cellular functions at multiple cellular locations, including the plasma membrane, where β-catenin contributes to the stabilization of intercellular adhesive complexes, the cytoplasm where β-catenin levels are regulated, and the nucleus where β-catenin is involved in transcriptional regulation and chromatin interactions.

Mutations in β-catenin (encoded by the CTNNB1 gene in humans) have been specifically associated with colorectal, desmoid, endometrial, gastric, hepatocellular, hepatoblastoma, kidney (Wilms' tumor), medulloblastoma, melanoma, ovarian (endometrioid), pancreatic, pilomatricoma, prostate, thyroid (anaplastic) and uterine (endometrium) cancers (Polakis P. Genes Dev. 14: 1837-51; Samowitz et al. Cancer Res. 59: 1442-4; Iwao et al. Cancer Res. 58: 1021-6; Mirabelli-Primdahl et al. Cancer Res. 59: 3346-51; Shitoh et al. J Clin Path. 52: 695-6; Tejpar et al. Oncogene 18: 6615-20; Kitaeva et al. Cancer Res. 57: 4478-81; Sparks et al. Cancer Res. 58: 1130-4; Miyaki et al. Cancer Res. 59: 4506-9; Park et al. Cancer Res. 59: 4257-60; Huang et al. Am J Pathol. 155: 1795-801; Nhieu et al. Am J Pathol. 155: 703-10; Legoix et al. Oncogene 18: 4044-6; Jeng et al. Cancer Lett. 152: 45-51; Koch et al. Cancer Res. 59: 269-73; Wei et al. Oncogene 19: 498-504; Koesters et al. Cancer Res. 59: 3880-2; Maiti et al. Cancer Res. 60: 6288-92; Zurawel et al. Cancer Res. 58: 896-9; Gamallo et al. Am J Pathol. 155: 527-36; Palacios and Gamallo Cancer Res. 58: 1344-7; Wright et al. Int J Cancer 82: 625-9; Gerdes et al. Digestion 60: 544-8; Chan et al. Nat Genet. 21: 410-3; Voeller et al. Cancer Res. 58: 2520-3; Garcia-Rostan et al. Cancer Res. 59: 1811-5; Fukuchi et al. Cancer Res. 58: 3526-8).

The β-catenin/Wnt pathway is consistently activated in over 80% of colorectal cancers. The β-catenin/Wnt pathway is also consistently activated in over 50% of hepatocellular carcinoma (HCC) patients. Activated Wnt signaling and nuclear β-catenin correlate with recurrence of disease and poor prognosis (Takigawa et al. 2008, Curr Drug Targets November; 9 (11):1013-24).

Mutations in the β-catenin gene include truncations that lead to deletion of part of the N-terminus of β-catenin or point mutations that affect the serine and threonine residues that are targeted by components of the cytoplasmic destruction complex, such as GSK3α/β or CKIα, that mediate the phosphorylation of β-catenin and target its degradation by the proteosome. These mutant β-catenin proteins are refractory to phosphorylation and thus escape proteasomal degradations. Consequently, β-catenin accumulates within affected cells. Stabilized and nuclear-localized β-catenin is a hallmark of nearly all cases of colon cancer. (Clevers, H., 2006, Cell 127:469-480). Morin et al. demonstrated that mutations of β-catenin that altered phosphorylation sites rendered the cells insensitive to APC-mediated down-regulation of β-catenin and that this disrupted mechanism was important to colorectal tumorigenesis. (Morin et al., 1997, Science 275:1787-1790).

Despite advances in understanding how β-catenin functions as a key mediator of Wnt signaling in cells and how mutations and/or altered expression of β-catenin can play a role in tumorigenesis, there remains a need for compositions that can be used to treat disease associated with CTNNB1 expression, such as cancer.

SUMMARY

This application provides a potent, optimized double-stranded β-catenin nucleic acid inhibitor molecule having a unique pattern of modified nucleotides, including a unique pattern of 2'-Fluoro ("2'-F") and 2'-O-methyl ("2'-OMe" or "2'-OCH$_3$") modifications at the 2'-carbon of the sugar moiety of the majority of nucleotides in the molecule. Without intending to be bound by any theory, it appears that the unique pattern of nucleotide modifications provides improved properties to the β-catenin nucleic acid inhibitor molecule, such as one or more of reduced immunogenicity, improved reduction of β-catenin mRNA expression, improved Ago2 binding, or improved inhibition of tumor growth.

In one embodiment, the optimized β-catenin nucleic acid inhibitor molecule comprises a sense (or passenger) strand comprising or consisting of the nucleic acid of SEQ ID NO: 11 and an antisense (or guide) strand comprising or consisting of the nucleic acid of SEQ ID NO: 12, and a region of complementarity between the sense strand and the antisense strand of 26 nucleotides. The antisense strand includes 2 single-stranded nucleotides at its 3' terminus and 10 single-stranded nucleotides at its 5' terminus. In certain embodiments, the sense strand consists of the nucleic acid of SEQ ID NO: 11 and the antisense strand consists of the nucleic acid of SEQ ID NO: 12.

In one embodiment, the optimized β-catenin nucleic acid inhibitor molecule is a double-stranded nucleic acid inhibitor molecule comprising a sense strand and an antisense strand;

wherein the sense strand comprises or consists of the nucleic acid sequence of SEQ ID NO: 13 and the antisense strand comprises or consists of the nucleic acid sequence of SEQ ID NO: 14 and the sense strand and antisense strand together form a duplex region of 26 base pairs and the antisense strand includes 2 single-stranded nucleotides at its 3' terminus and 10 single-stranded nucleotides at its 5' terminus;

wherein the sugar moiety of each of nucleotides 1, 3, 7, 9-11, 13, 15, 19, and 20 of SEQ ID NO: 13 is modified with a 2'-F, the sugar moiety of each of nucleotides 2, 4-6, 8, 12, 14, 16-18, and 24 of SEQ ID NO: 13 is modified with a 2'-OCH$_3$, nucleotides 25 and 26 of SEQ ID NO: 13 are deoxyribonucleotides, and nucleotides 21-23 of SEQ ID NO: 13 are ribonucleotides; and wherein the sugar moiety of each of nucleotides 2, 6, 19, 21, 23, 25, 30, 31, 33, and 35 of SEQ ID NO: 14 is modified with a 2'-F, the sugar moiety of each of nucleotides 1, 3-5, 7-9, 11-15, 20, 22, 24, 26, 32, 34, and 36-38 of SEQ ID NO: 14 is modified with a 2'-OCH$_3$, nucleotide 10 of SEQ ID NO: 14 is a deoxyribonucleotide, and nucleotides 16-18 and 27-29 of SEQ ID NO: 14 are ribonucleotides.

One aspect is directed to a method of treating cancer in a subject, comprising administering to the subject a therapeutically effective amount of the optimized β-catenin nucleic acid inhibitor molecule, as described herein. In certain embodiments, the method further comprises administering a therapeutically effective amount of an immunotherapeutic agent. In certain embodiments, the subject is a human.

Another aspect is directed to a pharmaceutical composition comprising the optimized β-catenin nucleic acid inhibitor molecule, as described herein. In certain embodiments, the pharmaceutical composition comprising the optimized β-catenin nucleic acid inhibitor molecule is for use in treating cancer. In certain embodiments, the pharmaceutical composition is administered in combination with an immunotherapeutic agent, such as an anti-CTLA-4 monoclonal antibody, an anti-PD-1 monoclonal antibody, an anti-PD-L1 monoclonal antibody, or a combination of an anti-CTLA-4 monoclonal antibody and an anti-PD-1 monoclonal antibody.

In certain embodiments of the method or the pharmaceutical composition, the cancer is a non-Wnt activated cancer. In other embodiments, the cancer is a Wnt activated cancer. In certain embodiments of the method or the pharmaceutical composition, the non-Wnt activated cancer is a melanoma, a neuroblastoma, or a renal cancer.

In certain embodiments of the method or composition, the optimized β-catenin nucleic acid inhibitor molecule, as described herein, is formulated with a lipid nanoparticle. In certain embodiments, the lipid nanoparticle comprises core lipids and envelope lipids, wherein the core lipids comprise a first cationic lipid and a first pegylated lipid and wherein the envelope lipids comprise a second cationic lipid, a neutral lipid, a sterol, and a second pegylated lipid. In certain embodiments, the first cationic lipid is DL-048, the first pegylated lipid is DSG-MPEG, the second cationic lipid is DL-103, the neutral lipid is DSPC, the sterol is cholesterol, and the second pegylated lipid is DSPE-MPEG.

BRIEF DESCRIPTION OF THE DRAWINGS

The accompanying drawings, which are incorporated in and constitute a part of this specification, illustrate certain embodiments, and together with the written description, serve to explain certain principles of the compositions and methods disclosed herein.

FIG. 2A schematically shows the structures of three, exemplary extended double-stranded nucleic acid inhibitor molecules that target the beta-catenin gene and have different nucleotide modification patterns: Extended M1 (EX M1); Extended M2 (EX M2); and Extended M3 (EX M3). In this schematic, unshaded nucleotides represent ribonucleic acid bases, striped nucleotides represent 2'-OMe modified bases, shaded bases represent 2'-F modified bases, and nucleotides outlined with black boxes represent deoxyribonucleic acid bases. The passenger and guide strands of EX M1 correspond to SEQ ID NO: 7 and SEQ ID NO: 8, respectively. The passenger and guide strands of EX M2 correspond to SEQ ID NO: 9 and SEQ ID NO: 10, respectively. The passenger and guide strands of EX M3 correspond to SEQ ID NO: 11 and SEQ ID NO: 12, respectively. Also shown are the IC50 values (pM) for the three molecules.

FIG. 2B shows the interferon response (as measured by IFIT1 induction) of different extended double-stranded nucleic acid inhibitor molecules in human peripheral blood mononuclear cells (PBMCs). EX M1 induced significant elevation of IF1T1 while EX M2 showed moderate elevation. NEX M3, on the other hand, showed essentially no elevation of IFIT1.

FIG. 4A shows that in mice bearing LS411N tumors and treated with NEX M1 and EX M3, EX M3 was present at much higher levels in tumor tissue at day 3 after dosing.

FIG. 4B shows that in mice bearing LS411N tumors and treated with NEX M1 and EX M3, EX M3 exhibited increased Argonaute (Ago) 2 binding/RNA-induced silencing complex (RISC) loading efficiencies in tumor tissue at day 3 after dosing.

FIG. 4C shows that in mice bearing SW403 tumors and treated with NEX M1 and EX M3, NEX M1 inhibited tumor growth by about 55% relative to vehicle-treated animals, whereas EX M3 inhibited tumor growth by over 80%. The x-axis lists the days post-implant (of SW403 tumors) with the arrows indicating the days on which NEX M1, EX M3, or control was administered (at a dosage of 3 mg/kg).

FIG. 4D shows by immunohistochemistry that there was a substantial decrease in beta-catenin protein levels in SW403 tumors obtained at the end of the study depicted in FIG. 4C.

FIG. 7A shows the treatment schedule for Balb/C mice that were implanted with Wnt-activated, 4T1 tumors and treated with placebo or EX M3, as described in Example 5.

FIG. 7B shows by immunohistochemistry that EX M3 treatment decreases β-catenin levels and increases CD8 T-cell infiltration but does not significantly reduce IDO1 levels in 4T1 tumors.

FIG. 7C shows that two cycles of EX M3 treatment inhibits tumor growth as compared to placebo in 4T1 tumors that were implanted into Balb/C mice.

FIG. 9A shows the treatment schedule for Balb/C mice that were implanted with 4T1 tumors and treated with vehicle or an IDO inhibitor (IDOi) called epacadostat, as described in Example 6.

FIG. 9B shows by immunohistochemistry that IDOi treatment decreases β-catenin levels, increases CD8 T-cell infiltration, and decreases IDO1 levels in 4T1 tumors.

FIG. 9C shows that two cycles of IDOi treatment inhibits tumor growth as compared to placebo in 4T1 tumors that were implanted into Balb/C mice.

DEFINITIONS

Figures 1A, 1B:
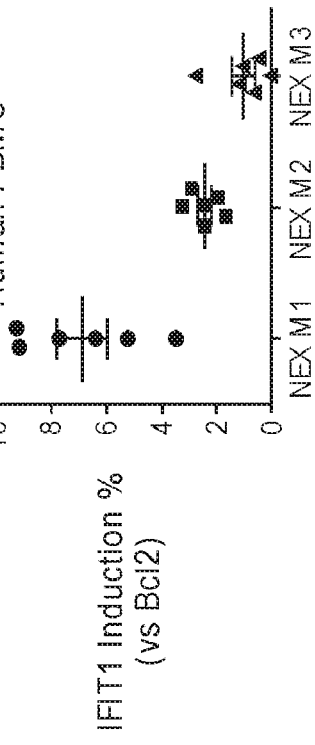
FIG. 1A schematically shows the structures of three, exemplary non-extended double-stranded nucleic acid inhibitor molecules that target the β-catenin gene and have different nucleotide modification patterns: NonExtended M1 (NEX M1); NonExtended M2 (NEX M2); and NonExtended M3 (NEX M3). In this schematic, unshaded nucleotides represent ribonucleotides, striped nucleotides contain 2'-OMe modifications, shaded bases contain 2'-F modifications, and nucleotides outlined with black boxes represent deoxyribonucleotides. The passenger and guide strands of NEX M1 correspond to SEQ ID NO: 1 and SEQ ID NO: 2, respectively. The passenger and guide strands of NEX M2 correspond to SEQ ID NO: 3 and SEQ ID NO: 4, respectively. The passenger and guide strands of NEX M3 correspond to SEQ ID NO: 5 and SEQ ID NO: 6, respectively. Also shown are the IC50 values (pM) for the three molecules.
FIG. 1B shows the interferon response (as measured by IFIT1 induction) of different non-extended double-stranded nucleic acid inhibitor molecules in human peripheral blood mononuclear cells (PBMCs). NEX M1 induced significant elevation of IF1T1 while NEX M2 showed moderate elevation. NEX M3, on the other hand, showed only minimal elevation of IFIT1.

In order for the present disclosure to be more readily understood, certain terms are first defined below. Additional definitions for the following terms and other terms may be set forth through the specification. If a definition of a term set forth below is inconsistent with a definition in an application or patent that is incorporated by reference, the definition set forth in this application should be used to understand the meaning of the term.

As used in this specification and the appended claims, the singular forms "a," "an," and "the" include plural references unless the context clearly dictates otherwise. Thus for example, a reference to "a method" includes one or more methods, and/or steps of the type described herein and/or which will become apparent to those persons skilled in the art upon reading this disclosure and so forth.

Administer: As used herein, "administering" a composition to a subject means to give, apply or bring the composition into contact with the subject. Administration can be accomplished by any of a number of routes, including, for example, topical, oral, subcutaneous, intramuscular, intraperitoneal, intravenous, intrathecal and intradermal.

Antibody: As used herein, the term "antibody" refers to an immunoglobulin or an antigen-binding domain thereof. The term includes but is not limited to polyclonal, monoclonal, monospecific, polyspecific, non-specific, humanized, human, single-chain, chimeric, synthetic, recombinant, hybrid, mutated, grafted, and in vitro generated antibodies. The antibody can include a constant region, or a portion thereof, such as the kappa, lambda, alpha, gamma, delta, epsilon and mu constant region genes. For example, heavy chain constant regions of the various isotypes can be used, including: $IgG_1$, $IgG_2$, $IgG_3$, $IgG_4$, IgM, $IgA_1$, $IgA_2$, IgD, and IgE. By way of example, the light chain constant region can be kappa or lambda.

Antigen-Binding Domain: As used herein, the term "antigen-binding domain" refers to a part of an antibody molecule that comprises amino acids responsible for the specific binding between antibody and antigen. For certain antigens, the antigen-binding domain may only bind to a part of the antigen. The part of the antigen that is specifically recognized and bound by the antibody is referred to as the "epitope" or "antigenic determinant." Antigen-binding domains include Fab (Fragment antigen-binding); a F(ab')$_2$ fragment, a bivalent fragment having two Fab fragments linked by a disulfide bridge at the hinge region; Fv fragment; a single chain $F_v$ fragment (scFv) see e.g., Bird et al. (1988) Science 242:423-426; and Huston et al. (1988) Proc. Natl. Acad. Sci. USA 85:5879-5883); a Fd fragment having the two $V_H$ and $C_H1$ domains; dAb (Ward et al., (1989) Nature 341:544-546), and other antibody fragments that retain antigen-binding function. The Fab fragment has $V_H$-$C_H1$ and $V_L$-$C_L$ domains covalently linked by a disulfide bond between the constant regions. The $F_v$ fragment is smaller and has $V_H$ and $V_L$ domains non-covalently linked. To overcome the tendency of non-covalently linked domains to dissociate, a $scF_v$ can be constructed. The $scF_v$ contains a flexible polypeptide that links (1) the C-terminus of $V_H$ to the N-terminus of $V_L$, or (2) the C-terminus of $V_L$ to the N-terminus of $V_H$. A 15-mer $(Gly_4Ser)_3$ peptide may be used as a linker, but other linkers are known in the art. These antibody fragments are obtained using conventional techniques known to those with skill in the art, and the fragments are evaluated for function in the same manner as are intact antibodies.

Antisense strand: A double-stranded nucleic acid inhibitor molecule comprises two oligonucleotide strands: an antisense strand and a sense strand. The antisense strand or a region thereof is partially, substantially or fully complementary to a corresponding region of a target nucleic acid. In addition, the antisense strand of the double-stranded nucleic acid inhibitor molecule or a region thereof is partially, substantially or fully complementary to the sense strand of the double-stranded nucleic acid inhibitor molecule or a region thereof. In certain embodiments, the antisense strand may also contain nucleotides that are non-complementary to the target nucleic acid sequence. The non-complementary nucleotides may be on either side of the complementary sequence or may be on both sides of the complementary sequence. In certain embodiments, where the antisense strand or a region thereof is partially or substantially complementary to the sense strand or a region thereof, the non-complementary nucleotides may be located between one or more regions of complementarity (e.g., one or more mismatches). The antisense strand of a double-stranded nucleic acid inhibitor molecule is also referred to as the guide strand.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

β-catenin: As used herein, "β-catenin" refers either to a polypeptide or a nucleic acid sequence encoding such a β-catenin protein. When referring to a polypeptide, "β-catenin" refers to the polypeptide gene product of a β-catenin gene/transcript (CTNNB1) (Genbank Accession Nos. NM_001904.3 (human β-catenin transcript variant 1), NM_001098209.1 (human β-catenin transcript variant 2), NM_001098210.1 (human β-catenin transcript variant 3), and NM_007614.2 & NM_007614.3 (mouse β-catenin).

Complementary: As used herein, the term "complementary" refers to a structural relationship between two nucleotides (e.g., on two opposing nucleic acids or on opposing regions of a single nucleic acid strand) that permits the two nucleotides to form base pairs with one another. For example, a purine nucleotide of one nucleic acid that is complementary to a pyrimidine nucleotide of an opposing nucleic acid may base pair together by forming hydrogen bonds with one another. In some embodiments, complementary nucleotides can base pair in the Watson-Crick manner or in any other manner that allows for the formation of stable duplexes. "Fully complementary" or 100% complementarity refers to the situation in which each nucleotide monomer of a first oligonucleotide strand or of a segment of a first oligonucleotide strand can form a base pair with each nucleotide monomer of a second oligonucleotide strand or of a segment of a second oligonucleotide strand. Less than 100% complementarity refers to the situation in which some, but not all, nucleotide monomers of two oligonucleotide strands (or two segments of two oligonucleotide strands) can form base pairs with each other. "Substantial complementarity" refers to two oligonucleotide strands (or segments of two oligonucleotide strands) exhibiting 90% or greater complementarity to each other. "Sufficiently complementary" refers to complementarity between a target mRNA and a nucleic acid inhibitor molecule, such that there is a reduction in the amount of protein encoded by a target mRNA.

Complementary strand: As used herein, the term "complementary strand" refers to a strand of a double-stranded nucleic acid inhibitor molecule that is partially, substantially or fully complementary to the other strand.

Deoxyribofuranosyl: As used herein, the term "deoxyribofuranosyl" refers to a furanosyl that is found in naturally occurring DNA and has a hydrogen group at the 2'-carbon, as illustrated below:

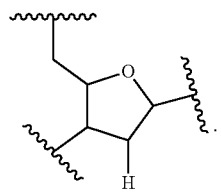 [SMILES: *CC1OC(*)CC1*]

Deoxyribonucleotide: As used herein, the term "deoxyribonucleotide" refers to a natural nucleotide (as defined herein) or a modified nucleotide (as defined herein) which has a hydrogen group at the 2'-position of the sugar moiety.

dsRNAi inhibitor molecule: As used herein, the term "dsRNAi inhibitor molecule" refers to a double-stranded nucleic acid inhibitor molecule having a sense strand (passenger) and antisense strand (guide), where the antisense strand or part of the antisense strand is used by the Argonaute 2 (Ago2) endonuclease in the cleavage of a target mRNA.

Duplex: As used herein, the term "duplex," in reference to nucleic acids (e.g., oligonucleotides), refers to a structure formed through complementary base pairing of two antiparallel sequences of nucleotides.

Excipient: As used herein, the term "excipient" refers to a non-therapeutic agent that may be included in a composition, for example to provide or contribute to a desired consistency or stabilizing effect.

Furanosyl: As used herein, the term "furanosyl" refers to a structure comprising a 5-membered ring with four carbon atoms and one oxygen atom.

Internucleotide linking group: As used herein, the term "internucleotide linking group" or "internucleotide linkage" refers to a chemical group capable of covalently linking two nucleoside moieties. Typically, the chemical group is a phosphorus-containing linkage group containing a phospho or phosphite group. Phospho linking groups are meant to include a phosphodiester linkage, a phosphorodithioate linkage, a phosphorothioate linkage, a phosphotriester linkage, a thionoalkylphosphonate linkage, a thionalkylphosphotriester linkage, a phosphoramidite linkage, a phosphonate linkage and/or a boranophosphate linkage. Many phosphorus-containing linkages are well known in the art, as disclosed, for example, in U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050. In other embodiments, the oligonucleotide contains one or more internucleotide linking groups that do not contain a phosphorous atom, such short chain alkyl or cycloalkyl internucleotide linkages, mixed heteroatom and alkyl or cycloalkyl internucleotide linkages, or one or more short chain heteroatomic or heterocyclic internucleotide linkages, including, but not limited to, those having siloxane backbones; sulfide, sulfoxide and sulfone backbones; formacetyl and thioformacetyl backbones; methylene formacetyl and thioformacetyl backbones;

riboacetyl backbones; alkene containing backbones; sulfamate backbones; methyleneimino and methylenehydrazino backbones; sulfonate and sulfonamide backbones; and amide backbones. Non-phosphorous containing linkages are well known in the art, as disclosed, for example, in U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439.

Immune checkpoint molecules: As used herein, the term "immune checkpoint molecule" refers to molecules on immune cells, such as T cells, that are important under normal physiological conditions for the maintenance of self-tolerance (or the prevention of autoimmunity) and the protection of host cells and tissue when the immune system responds to a foreign pathogen. Certain immune checkpoint molecules are co-stimulatory molecules that amplify a signal involved in the T cell response to antigen while certain immune checkpoint molecules are inhibitory molecules (e.g., CTLA-4 or PD-1) that reduce a signal involved in the T cell response to antigen.

Modified nucleobase: As used herein, the term "modified nucleobase" refers to any nucleobase that is not a natural nucleobase or a universal nucleobase. Suitable modified nucleobases include diaminopurine and its derivatives, alkylated purines or pyrimidines, acylated purines or pyrimidines thiolated purines or pyrimidines, and the like. Other suitable modified nucleobases include analogs of purines and pyrimidines. Suitable analogs include, but are not limited to, 1-methyladenine, 2-methyladenine, N6-methyladenine, N6-isopentyladenine, 2-methylthio-N6-isopentyladenine, N,N-dimethyladenine, 8-bromoadenine, 2-thiocytosine, 3-methylcytosine, 5-methylcytosine, 5-ethylcytosine, 4-acetylcytosine, 1-methylguanine, 2-methylguanine, 7-methylguanine, 2,2-dimethylguanine, 8-bromoguanine, 8-chloroguanine, 8-aminoguanine, 8-methylguanine, 8-thioguanine, 5-fluorouracil, 5-bromouracil, 5-chlorouracil, 5-iodouracil, 5-ethyluracil, 5-propyluracil, 5-methoxyuracil, 5-hydroxymethyluracil, 5-(carboxyhydroxymethyl)uracil, 5-(methylaminomethyl)uracil, 5-(carboxymethylaminomethyl)-uracil, 2-thiouracil, 5-methyl-2-thiouracil, 5-(2-bromovinyl)uracil, uracil-5-oxyacetic acid, uracil-5-oxyacetic acid methyl ester, pseudouracil, 1-methylpseudouracil, queosine, hypoxanthine, xanthine, 2-aminopurine, 6-hydroxyaminopurine, nitropyrrolyl, nitroindolyl and difluorotolyl, 6-thiopurine and 2,6-diaminopurine nitropyrrolyl, nitroindolyl and difluorotolyl. Typically a nucleobase contains a nitrogenous base. In certain embodiments, the nucleobase does not contain a nitrogen atom. See e.g., U.S. Published Patent Application No. 20080274462.

Modified nucleoside: As used herein, the term "modified nucleoside" refers to a heterocyclic nitrogenous base in N-glycosidic linkage with a sugar (e.g., deoxyribose or ribose or analog thereof) that is not linked to a phosphate group or a modified phosphate group (as defined herein) and that contains one or more of a modified nucleobase (as defined herein), a universal nucleobase (as defined herein) or a modified sugar moiety (as defined herein). The modified or universal nucleobases (also referred to herein as base analogs) are generally located at the 1'-position of a nucleoside sugar moiety and refer to nucleobases other than adenine, guanine, cytosine, thymine and uracil at the 1'-position. In certain embodiments, the modified or universal nucleobase is a nitrogenous base. In certain embodiments, the modified nucleobase does not contain nitrogen atom. See e.g., U.S. Published Patent Application No. 20080274462. In certain embodiments, the modified nucleotide does not contain a nucleobase (abasic). Suitable modified or universal nucleobases or modified sugars in the context of the present disclosure are described herein.

Modified nucleotide: As used herein, the term "modified nucleotide" refers to a heterocyclic nitrogenous base in N-glycosidic linkage with a sugar (e.g., ribose or deoxyribose or analog thereof) that is linked to a phosphate group or a modified phosphate group (as defined herein) and contains one or more of a modified nucleobase (as defined herein), a universal nucleobase (as defined herein), or a modified sugar moiety (as defined herein). The modified or universal nucleobases (also referred to herein as base analogs) are generally located at the 1'-position of a nucleoside sugar moiety and refer to nucleobases other than adenine, guanine, cytosine, thymine and uracil at the 1'-position. In certain embodiments, the modified or universal nucleobase is a nitrogenous base. In certain embodiments, the modified nucleobase does not contain nitrogen atom. See e.g., U.S. Published Patent Application No. 20080274462. In certain embodiments, the modified nucleotide does not contain a nucleobase (abasic). Suitable modified or universal nucleobases, modified sugar moieties, or modified phosphate groups in the context of the present disclosure are described herein.

Modified phosphate group: As used herein, the term "modified phosphate group" refers to a modification of the phosphate group that does not occur in natural nucleotides and includes non-naturally occurring phosphate mimics as described herein, including phosphate mimics that include a phosphorous atom and anionic phosphate mimics that do not include phosphate (e.g. acetate). Modified phosphate groups also include non-naturally occurring internucleotide linking groups, including both phosphorous-containing internucleotide linking groups, including, for example, phosphorothioate, and non-phosphorous containing linking groups, as described herein.

Modified sugar moiety: As used herein, a "modified sugar moiety" refers to a substituted sugar moiety (as defined herein) or a sugar analog (as defined herein).

Natural nucleoside: As used herein, the term "natural nucleoside" refers to a heterocyclic nitrogenous base in N-glycosidic linkage with a sugar (e.g., deoxyribose or ribose or analog thereof). The natural heterocyclic nitrogenous bases include adenine, guanine, cytosine, uracil and thymine.

Natural nucleotide: As used herein, the term "natural nucleotide" refers to a heterocyclic nitrogenous base in N-glycosidic linkage with a sugar (e.g., ribose or deoxyribose or analog thereof) that is linked to a phosphate group. The natural heterocyclic nitrogenous bases include adenine, guanine, cytosine, uracil and thymine.

Natural nucleobase: As used herein, the term "natural nucleobase" refers to the five primary, naturally occurring heterocyclic nucleobases of RNA and DNA, i.e., the purine bases: adenine (A) and guanine (G), and the pyrimidine bases: thymine (T), cytosine (C), and uracil (U).

Natural nucleoside: As used herein, the term "natural nucleoside" refers to a natural nucleobase (as defined herein) in N-glycosidic linkage with a natural sugar moiety (as defined herein) that is not linked to a phosphate group.

Natural nucleotide: As used herein, the term "natural nucleotide" refers to a natural nucleobase (as defined herein) in N-glycosidic linkage with a natural sugar moiety (as defined herein) that is linked to a phosphate group.

Natural sugar moiety: As used herein, the term "natural sugar moiety" refers to a ribofuranosyl (as defined herein) or a deoxyribofuranosyl (as defined herein).

non-T cell inflamed phenotype: As used herein, "non-T cell inflamed phenotype" refers to a tumor microenvironment without a pre-existing T cell response against the tumor, as evidenced by little to no accumulation of infiltrating CD8+ T cells in the tumor microenvironment. Typically, the non-T cell inflamed phenotype is also characterized by a limited chemokine profile that does not promote the recruitment and accumulation of CD8+ T cells in the tumor microenvironment and/or a minimal or absent type I IFN gene signature.

non-Wnt activated disease or disorder: As used herein, a "non-Wnt activated" disease or disorder refers to a disease or disorder that is not associated with activation of the Wnt/β-catenin pathway. A "non-Wnt activated" disease or disorder includes certain cancer and/or proliferative diseases, conditions, or disorders, including certain colorectal, desmoid, endometrial, gastric, hepatocellular, hepatoblastoma, kidney (Wilms' tumor), medulloblastoma, melanoma, neuroblastoma, ovarian (endometrioid), pancreatic, pilomatricoma, prostate, renal, thyroid (anaplastic) and uterine (endometrium) cancers. In one embodiment, the "non-Wnt activated" disease or disorder is colorectal cancer, hepatocellular carcinoma, or melanoma. In one embodiment, the "non-Wnt activated" disease or disorder is neuroblastoma, renal cancer, or melanoma. It is understood that a disease or disorder, including the cancer and/or proliferative diseases listed above, may include both a non-Wnt activated sub-type of the disease or disorder and a Wnt activated sub-type of the disease or disorder, consistent with the definition of Wnt activated disease or disorder provided below.

Nucleic acid inhibitor molecule: As used herein, the term "nucleic acid inhibitor molecule" refers to an oligonucleotide molecule that reduces or eliminates the expression of a target gene wherein the oligonucleotide molecule contains a region that specifically targets a sequence in the target gene mRNA. Typically, the targeting region of the nucleic acid inhibitor molecule comprises a sequence that is sufficiently complementary to a sequence on the target gene mRNA to direct the effect of the nucleic acid inhibitor molecule to the specified target gene. The nucleic acid inhibitor molecule may include ribonucleotides, deoxyribonucleotides, and/or modified nucleotides.

Nucleobase: As used herein, the term "nucleobase" refers to a natural nucleobase (as defined herein), a modified nucleobase (as defined herein), or a universal nucleobase (as defined herein).

Nucleoside: As used herein, the term "nucleoside" refers to a natural nucleoside (as defined herein) or a modified nucleoside (as defined herein).

Nucleotide: As used herein, the term "nucleotide" refers to a natural nucleotide (as defined herein) or a modified nucleotide (as defined herein).

Overhang: As used herein, the term "overhang" refers to terminal non-base pairing nucleotide(s) at either end of either strand of a double-stranded nucleic acid inhibitor molecule. In certain embodiments, the overhang results from one strand or region extending beyond the terminus of the complementary strand to which the first strand or region forms a duplex. One or both of two oligonucleotide regions that are capable of forming a duplex through hydrogen bonding of base pairs may have a 5'- and/or 3'-end that extends beyond the 3'- and/or 5'-end of complementarity shared by the two polynucleotides or regions. The single-stranded region extending beyond the 3'- and/or 5'-end of the duplex is referred to as an overhang.

Pharmaceutical composition: As used herein, the term "pharmaceutical composition" comprises a pharmacologically effective amount of a β-catenin nucleic acid inhibitor molecule or an immunotherapeutic agent, such as an antibody (including, for example, one or more of an anti-CTLA-4, anti-PD-1, or anti-PD-L1 antibody) and a pharmaceutically acceptable excipient.

Pharmaceutically acceptable excipient: As used herein, the term "pharmaceutically acceptable excipient" means that the excipient is one that is suitable for use with humans and/or animals without undue adverse side effects (such as toxicity, irritation, and allergic response) commensurate with a reasonable benefit/risk ratio.

Phosphate mimic: As used herein, the term "phosphate mimic" refers to a chemical moiety at the 5'-terminal end of an oligonucleotide that mimics the electrostatic and steric properties of a phosphate group. Many phosphate mimics have been developed that can be attached to the 5'-end of an oligonucleotide (see, e.g., U.S. Pat. No. 8,927,513; Prakash et al. *Nucleic Acids Res.,* 2015, 43(6):2993-3011). Typically, these 5'-phosphate mimics contain phosphatase-resistant linkages. Suitable phosphate mimics include 5'-phosphonates, such as 5'-methylenephosphonate (5'-MP) and 5'-(E)-vinylphosphonate (5'-VP) and 4'-phosphate analogs that are bound to the 4'-carbon of the sugar moiety (e.g., a ribose or deoxyribose or analog thereof) of the 5'-terminal nucleotide of an oligonucleotide, such as 4'-oxymethylphosphonate, 4'-thiomethylphosphonate, or 4'-aminomethylphosphonate, as described in International Publication No. WO 2018/045317, which is hereby incorporated by reference in its entirety. In certain embodiments, the 4'-oxymethylphosphonate is represented by the formula —O—$CH_2$—PO(OH)$_2$ or —O—$CH_2$—PO(OR)$_2$, where R is independently selected from H, $CH_3$, an alkyl group, or a protecting group. In certain embodiments, the alkyl group is $CH_2CH_3$. More typically, R is independently selected from H, $CH_3$, or $CH_2CH_3$. Other modifications have been developed for the 5'-end of oligonucleotides (see, e.g., WO 2011/133871).

Potentiate: The term "potentiate" or "potentiating" as used herein refers to the ability of one therapeutic agent (e.g., a β-catenin nucleic acid inhibitor molecule) to increase or enhance the therapeutic effect of another therapeutic agent (e.g., an antagonist of an inhibitory immune checkpoint molecule, such as CTLA-4 or PD-1, or an agonist of a co-stimulatory checkpoint molecule).

Protecting group: As used herein, the term "protecting group" is used in the conventional chemical sense as a group which reversibly renders unreactive a functional group under certain conditions of a desired reaction. After the desired reaction, protecting groups may be removed to deprotect the protected functional group. All protecting groups should be removable under conditions which do not degrade a substantial proportion of the molecules being synthesized.

Reduce(s): The term "reduce" or "reduces" as used herein refers to its meaning as is generally accepted in the art. With reference to nucleic acid inhibitor molecules, the term generally refers to the reduction in the expression of a gene, or level of RNA molecules or equivalent RNA molecules encoding one or more proteins or protein subunits, or activity of one or more proteins or protein subunits, below that observed in the absence of the nucleic acid inhibitor molecules.

Resistance: The term "resistance" or "resistant" as used in relation to immunotherapy refers to a cancer and/or proliferative disease, condition or disorder that does not show a medically significant response to immunotherapy. As disclosed herein, resistance to immunotherapy can be reversed by reducing β-catenin expression.

Ribofuranosyl: As used herein, the term "ribofuranosyl" refers to a furanosyl that is found in naturally occurring RNA and has a hydroxyl group at the 2'-carbon, as illustrated below:

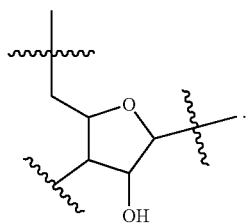 [SMILES: *CC1OC(*)C(O)C1*]

Ribonucleotide: As used herein, the term "ribonucleotide" refers to a natural nucleotide (as defined herein) or a modified nucleotide (as defined herein) which has a hydroxyl group at the 2'-position of the sugar moiety.

Sense strand: A double-stranded nucleic acid inhibitor molecule comprises two oligonucleotide strands: an antisense strand and a sense strand. The sense strand or a region thereof is partially, substantially or fully complementary to the antisense strand of the double-stranded nucleic acid inhibitor molecule or a region thereof. In certain embodiments, the sense strand may also contain nucleotides that are non-complementary to the antisense strand. The non-complementary nucleotides may be on either side of the complementary sequence or may be on both sides of the complementary sequence. In certain embodiments, where the sense strand or a region thereof is partially or substantially complementary to the antisense strand or a region thereof, the non-complementary nucleotides may be located between one or more regions of complementarity (e.g., one or more mismatches). The sense strand is also called the passenger strand.

Subject: As used herein, the term "subject" means any mammal, including mice, rabbits, and humans. In one embodiment, the subject is a human. The terms "individual" or "patient" are intended to be interchangeable with "subject."

Substituent or substituted: The terms "substituent" or "substituted" as used herein refer to the replacement of hydrogen radicals in a given structure with the radical of a substituent. When more than one position in any given structure may be substituted with more than one substituent, the substituent may be either the same or different at every position unless otherwise indicated. As used herein, the term "substituted" is contemplated to include all permissible substituents that are compatible with organic compounds. The permissible substituents include acyclic and cyclic, branched and unbranched, carbocyclic and heterocyclic, aromatic and nonaromatic substituents of organic compounds. This disclosure is not intended to be limited in any manner by the permissible substituents of organic compounds.

Substituted sugar moiety: As used herein, a "substituted sugar moiety" includes furanosyls comprising one or more modifications. Typically, the modifications occur at the 2'-, 3'-, 4'-, or 5'-carbon position of the sugar.

Sugar analog: As used herein, the term "sugar analog" refers to a structure that does not comprise a furanosyl and that is capable of replacing the naturally occurring sugar moiety of a nucleotide, such that the resulting nucleotide is capable of (1) incorporation into an oligonucleotide and (2) hybridization to a complementary nucleotide. Such structures typically include relatively simple changes to the furanosyl, such as rings comprising a different number of atoms (e.g., 4, 6, or 7-membered rings); replacement of the oxygen of the furanosyl with a non-oxygen atom (e.g., carbon, sulfur, or nitrogen); or both a change in the number of atoms and a replacement of the oxygen. Such structures may also comprise substitutions corresponding with those described for substituted sugar moieties. Sugar analogs also include more complex sugar replacements (e.g., the non-ring systems of peptide nucleic acid). Sugar analogs include without limitation morpholinos, cyclohexenyls and cyclohexitols.

Sugar moiety: As used herein, the term "sugar moiety" refers to a natural sugar moiety or a modified sugar moiety of a nucleotide or nucleoside.

Target site: As used herein, the term "target site" "target sequence," "target nucleic acid", "target region," "target gene" are used interchangeably and refer to a RNA or DNA sequence that is "targeted," e.g., for cleavage mediated by a dsRNAi inhibitor molecule that contains a sequence within its guide/antisense region that is partially, substantially, or perfectly or sufficiently complementary to that target sequence.

T cell-inflamed tumor phenotype: As used herein, "T cell-inflamed phenotype" refers to a tumor microenvironment with a pre-existing T cell response against the tumor, as evidenced by an accumulation of infiltrating CD8+ T cells in the tumor microenvironment. Typically, the T cell-inflamed phenotype is also characterized by a broad chemokine profile capable of recruiting CD8+ T cells to the tumor microenvironment (including CXCL9 and/or CXCL10) and/or a type I IFN gene signature.

Therapeutically effective amount: As used herein, a "therapeutically effective amount" or "pharmacologically effective amount" refers to that amount of a β-catenin nucleic acid inhibitor molecule or an immunotherapeutic agent, such as an antibody (including, for example, one or more of an anti-CTLA-4, anti-PD-1, or anti-PD-L1 antibody) effective to produce the intended pharmacological, therapeutic or preventive result.

Universal nucleobase: As used herein, a "universal nucleobase" refers to a base that can pair with more than one of the bases typically found in naturally occurring nucleic acids and can thus substitute for such naturally occurring bases in a duplex. The base need not be capable of pairing with each of the naturally occurring bases. For example, certain bases pair only or selectively with purines, or only or selectively with pyrimidines. The universal nucleobase may base pair by forming hydrogen bonds via Watson-Crick or non-Watson-Crick interactions (e.g., Hoogsteen interactions). Representative universal nucleobases include inosine and its derivatives.

Wnt activated disease or disorder: As used herein, a "Wnt activated" disease or disorder refers to a disease or disorder that is associated with an activated Wnt/β-catenin pathway. A "Wnt-associated" disease or disorder includes cancer and/or proliferative diseases, conditions, or disorders, including colorectal, desmoid, endometrial, gastric, hepatocellular, hepatoblastoma, kidney (Wilms' tumor), medulloblastoma, melanoma, ovarian (endometrioid), pancreatic, pilomatricoma, prostate, thyroid (anaplastic) and uterine (endometrium) cancers. In one embodiment, the "Wnt activated" disease or disorder is colorectal cancer, hepatocellular carcinoma, or melanoma. It is understood that a disease or disorder, including the cancer and/or proliferative diseases listed above, may include both a Wnt activated version of the disease or disorder and a non-Wnt activated version of the disease or disorder, consistent with the definition of non-Wnt activated disease or disorder provided above.

Figure 6:
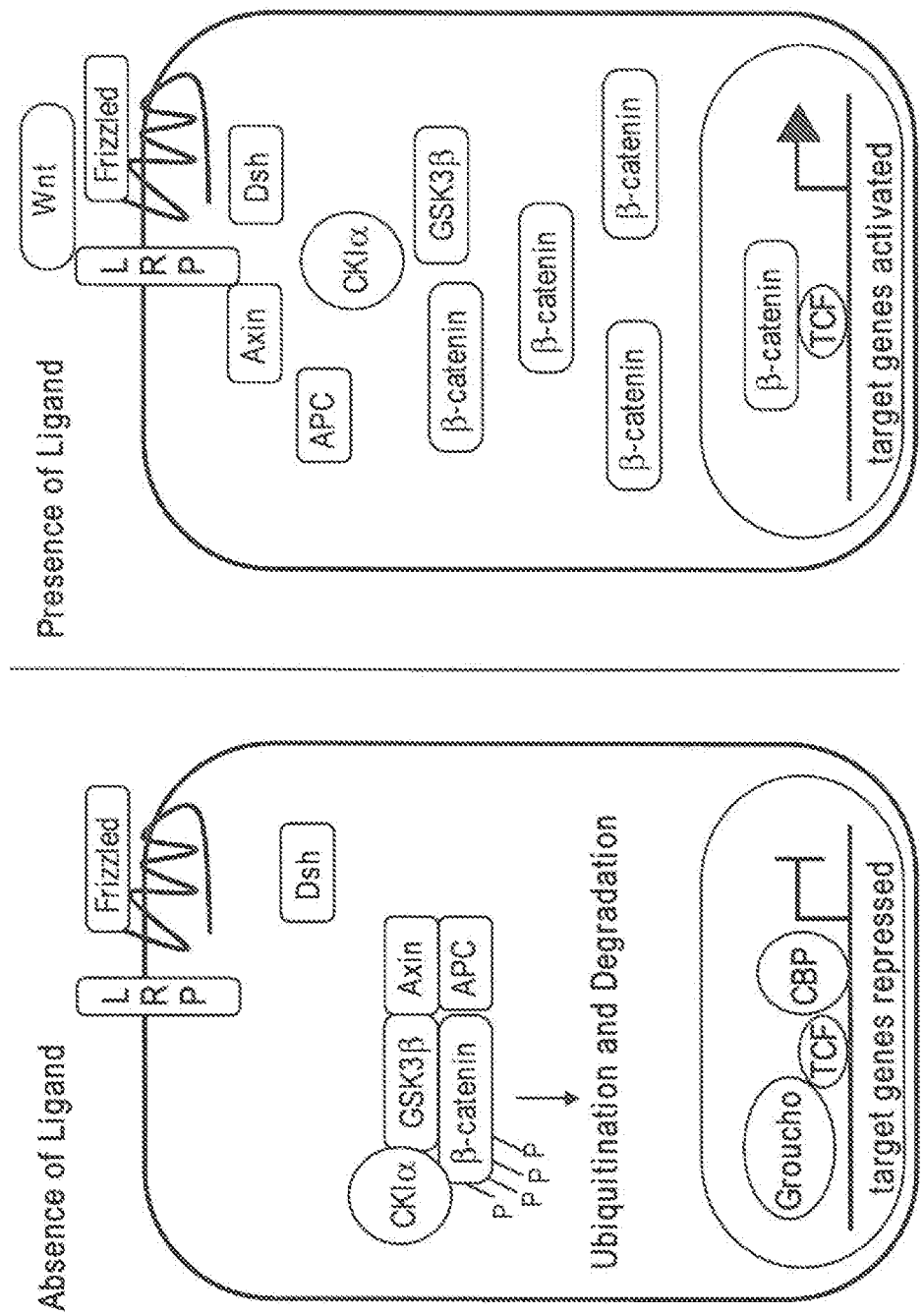
FIG. 6 shows a simplified diagram of the Wnt signaling pathway. The left side depicts a cell where the Wnt ligand is not bound to its surface receptor, β-catenin is sequestered in a destruction complex and targeted for ubiquitination and degradation, and target genes are repressed. The right side depicts a cell after the Wnt ligand has bound its surface receptor, where the destruction complex disassembles, stabilized β-catenin is released and travels to the nucleus, and target genes are activated.

Wnt/β-catenin pathway: As used herein the "Wnt/β-catenin pathway" refers to a molecular signaling pathway in cells that is mediated through a combination of Wnt ligands, receptors, and co-receptors, which initiate a downstream signaling pathway that involves β-catenin (see e.g., FIG. 6). In the absence of Wnt signaling, β-catenin is targeted for degradation via ubiquitination in the cellular cytoplasm. In the presence of Wnt ligand and Wnt signaling, β-catenin is stabilized and travels to the cell nucleus where it can interact with transcription factors, such as T cell transcription factor (TCF) and lymphoid enhanced transcription factor (LEF), and activate gene transcription. Deregulation and activation of the Wnt/β-catenin pathway is most often caused by mutations in the β-catenin gene or the gene encoding adenomatous polyposis coli (APC), which negatively regulates β-catenin function, but can also be caused by a mutation in a gene encoding other components of the Wnt/β-catenin pathway, such as Axin, LEF, and ICAT.

DETAILED DESCRIPTION

This application provides a potent, optimized double-stranded β-catenin nucleic acid inhibitor molecule having a unique pattern of modified nucleotides. As shown in the examples, changing the modification patterns of the nucleotides in the sense and antisense strands of a double-stranded nucleic acid molecule can result in improved properties, including reduced immunogenicity and improved reduction of β-catenin mRNA expression in tumor cells, even when the nucleotide sequences of the sense and antisense strands are identical. Also provided are methods of using the optimized, double-stranded β-catenin nucleic acid inhibitor molecule and compositions comprising the same to reduce the level or expression of the β-catenin gene in vitro or in vivo, including methods and compositions for treating cancer, including cancer that is not responsive to immunotherapy (e.g., blockade of immune checkpoint molecules).

Optimized β-Catenin Nucleic Acid Inhibitor Molecule

The double-stranded β-catenin nucleic acid inhibitor molecule described herein comprises a unique pattern of nucleotide modifications and possesses improved properties relative to β-catenin nucleic acid inhibitor molecules that do not share the same pattern of nucleotide modifications. In certain embodiments, the sense strand of the optimized β-catenin nucleic acid inhibitor molecule comprises the nucleic acid of SEQ ID NO: 11. In certain embodiments, the sense strand of the optimized β-catenin nucleic acid inhibitor molecule consists of the nucleic acid of SEQ ID NO: 11. In certain embodiments, the antisense strand of the optimized β-catenin nucleic acid inhibitor molecule comprises the nucleic acid of SEQ ID NO: 12. In certain embodiments, the antisense strand of the optimized β-catenin nucleic acid inhibitor molecule consists of the nucleic acid of SEQ ID NO: 12. In one embodiment, the sense strand consists of the nucleic acid of SEQ ID NO: 11 and the antisense strand consists of the nucleic acid of SEQ ID NO: 12. In one embodiment, the sense strand comprises the nucleic acid of SEQ ID NO: 11 and the antisense strand comprises the nucleic acid of SEQ ID NO: 12.

In certain embodiments, the optimized β-catenin nucleic acid inhibitor molecule is a double-stranded nucleic acid inhibitor molecule comprising a sense strand and an antisense strand, wherein the sense strand comprises or consists of the nucleic acid of SEQ ID NO: 11 and the antisense strand comprises or consists of the nucleic acid of SEQ ID NO: 12 and the sense strand and antisense strand together form a duplex region of 26 base pairs, and wherein the antisense strand includes 2 single-stranded nucleotides at its 3' terminus and 10 single-stranded nucleotides at its 5' terminus.

A schematic of this optimized β-catenin nucleic acid inhibitor molecule is set forth in FIG. 2A ("EX M3"), showing the sequences of the sense and antisense strands, the region of complementarity between the sense and antisense strands, and the unique pattern of modified nucleotides.

The unique pattern of modified nucleotides is also set forth in SEQ ID NO: 11 and SEQ ID NO: 12. As set forth in SEQ ID NO: 11 and SEQ ID NO: 12, the sugar moiety of most of the nucleotides in the modified β-catenin nucleic acid inhibitor molecule is modified with either a 2'-F or a 2'-OCH$_3$. Specifically, for the sense strand (SEQ ID NO: 11), the sugar moiety of each of nucleotides 1, 3, 7, 9-11, 13, 15, 19, and 20 is modified with a 2'-F, and the sugar moiety of each of nucleotides 2, 4-6, 8, 12, 14, 16-18, and 24 of is modified with a 2'-OCH$_3$, as depicted in FIG. 2A. For the antisense strand (SEQ ID NO: 12), the sugar moiety of each of nucleotides 2, 6, 19, 21, 23, 25, 30, 31, 33, and 35 is modified with a 2'-F, and the sugar moiety of each of nucleotides 1, 3-5, 7-9, 11-15, 20, 22, 24, 26, 32, 34, and 36-38 is modified with a 2'-OCH$_3$, as depicted in FIG. 2. The remaining nucleotides in the optimized β-catenin nucleic acid inhibitor molecule are not modified with either a 2'-F or a 2'-OCH$_3$. More specifically, for the sense strand (SEQ ID NO: 11), nucleotides 25 and 26 are deoxyribonucleotides and nucleotides 21-23 are ribonucleotides. Typically, nucleotides 25 and 26 are natural deoxyribonucleotides and nucleotides 21-23 are natural ribonucleotides. For the antisense strand (SEQ ID NO: 12), nucleotide 10 is a deoxyribonucleotide and nucleotides 16-18 and 27-29 are ribonucleotides. Typically, nucleotide 10 is a natural deoxyribonucleotide and nucleotides 16-18 and 27-29 are natural ribonucleotides.

In one embodiment, the optimized β-catenin nucleic acid inhibitor molecule is a double-stranded nucleic acid inhibitor molecule comprising a sense strand and an antisense strand;

wherein the sense strand comprises or consists of the nucleic acid sequence of SEQ ID NO: 13 (agaauacaaaugauguagaaacagcc) and the antisense strand comprises or consists of the nucleic acid sequence of SEQ ID NO: 14 (uagcuaucgtggcuguuucuacaucauuuguauucugc) and the sense strand and antisense strand together form a duplex region of 26 base pairs and the antisense strand includes 2 single-stranded nucleotides at its 3' terminus and 10 single-stranded nucleotides at its 5' terminus;

wherein the sugar moiety of each of nucleotides 1, 3, 7, 9-11, 13, 15, 19, and 20 of SEQ ID NO: 13 is modified with a 2'-F, the sugar moiety of each of nucleotides 2, 4-6, 8, 12, 14, 16-18, and 24 of SEQ ID NO: 13 is modified with a 2'-OCH$_3$, nucleotides 25 and 26 of SEQ ID NO: 13 are natural deoxyribonucleotides, and nucleotides 21-23 of SEQ ID NO: 13 are natural ribonucleotides;

wherein the sugar moiety of each of nucleotides 2, 6, 19, 21, 23, 25, 30, 31, 33, and 35 of SEQ ID NO: 14 is modified with a 2'-F, the sugar moiety of each of nucleotides 1, 3-5, 7-9, 11-15, 20, 22, 24, 26, 32, 34, and 36-38 of SEQ ID NO: 14 is modified with a 2'-OCH$_3$, nucleotide 10 of SEQ ID NO: 14 is a natural deoxyribonucleotide, and nucleotides 16-18 and 27-29 of SEQ ID NO: 14 are natural ribonucleotides.

A related aspect is directed to an oligonucleotide comprising or consisting of the nucleic acid of SEQ ID NO: 11. Another aspect is directed to an oligonucleotide comprising or consisting of the nucleic acid of SEQ ID NO: 12.

Also provided is an oligonucleotide comprising or consisting of the nucleic acid of SEQ ID NO: 13, wherein the sugar moiety of each of nucleotides 1, 3, 7, 9-11, 13, 15, 19, and 20 is modified with a 2'-F; the sugar moiety of each of nucleotides 2, 4-6, 8, 12, 14, 16-18, and 24 is modified with a 2'-OCH$_3$; nucleotides 25 and 26 are deoxyribonucleotides; and nucleotides 21-23 are ribonucleotides. Typically, nucleotides 25 and 26 are natural deoxyribonucleotides and nucleotides 21-23 are natural ribonucleotides.

Also provided is an oligonucleotide comprising or consisting of the nucleic acid of SEQ ID NO: 14, wherein the sugar moiety of each of nucleotides 2, 6, 19, 21, 23, 25, 30, 31, 33, and 35 is modified with a 2'-F; the sugar moiety of each of nucleotides 1, 3-5, 7-9, 11-15, 20, 22, 24, 26, 32, 34, and 36-38 is modified with a 2'-OCH$_3$; nucleotide 10 is a deoxyribonucleotide; and nucleotides 16-18 and 27-29 are ribonucleotides. Typically, nucleotide 10 is a natural deoxyribonucleotide and nucleotides 16-18 and 27-29 are natural ribonucleotides.

Other Modifications

As described herein, the optimized β-catenin nucleic acid inhibitor molecule contains a unique pattern of nucleotide modifications, including a unique pattern of 2'-F and 2'-OMe modifications at the 2'-carbon of the sugar moiety of certain nucleotides, as set forth in SEQ ID NO: 11 and SEQ ID NO: 12.

In certain embodiments, the nucleotides of the optimized β-catenin nucleic acid inhibitor molecule contain one or more additional modifications that occur at other parts of the nucleotide, including the nucleobase, the phosphate group, or other parts of the sugar moiety.

For example, in certain embodiments, the ring structure of the sugar moiety can be modified, including, but not limited to, the modified ring structure present in Locked Nucleic Acids ("LNA") (see, e.g., Koshkin et al. (1998), *Tetrahedron*, 54, 3607-3630); Bridged Nucleic acids ("BNA") (see, e.g., U.S. Pat. No. 7,427,672 and Mitsuoka et al. (2009), *Nucleic Acids Res.*, 37(4):1225-38); and Unlocked Nucleic Acids ("UNA") (see, e.g., Snead et al. (2013), *Molecular Therapy—Nucleic Acids*, 2,e103(doi: 10.1038/mtna.2013.36)). Additional modifications can also occur at other parts of the sugar moiety of the nucleotide, such as the 5'-carbon, as described herein.

In certain embodiments, the optimized β-catenin nucleic acid inhibitor molecule can also include one or more modified nucleobases other than adenine, guanine, cytosine, thymine and uracil at the 1'-position, as known in the art and as described herein. In certain embodiments, the modified or universal nucleobase is a nitrogenous base. In certain embodiments, the modified nucleobase does not contain nitrogen atom. See e.g., U.S. Published Patent Application No. 20080274462. In certain embodiments, the modified nucleotide does not contain a nucleobase (abasic). A typical example of a modified nucleobase is 5'-methylcytosine.

In certain embodiments, the optimized β-catenin nucleic acid inhibitor molecule can also include one or more modified phosphate groups. A modified phosphate group refers to a modification of the phosphate group that does not occur in natural nucleotides and includes non-naturally occurring phosphate mimics as described herein, including phosphate mimics that include a phosphorous atom and anionic phosphate mimics that do not include phosphate (e.g. acetate). Modified phosphate groups also include non-naturally occurring internucleotide linking groups, including both phosphorous-containing internucleotide linking groups and non-phosphorous containing linking groups, as described herein. Typically, the optimized β-catenin nucleic acid inhibitor molecule contains one or more phosphorous-containing internucleotide linking groups, as described herein. In other embodiments, one or more of the internucleotide linking groups of the nucleic acid inhibitor molecule is a non-phosphorus containing linkage. In certain embodiments, the optimized β-catenin nucleic acid inhibitor molecule contains one or more phosphorous-containing internucleotide linking groups and one or more non-phosphorous containing internucleotide linking groups, as described herein.

The 5'-end of the nucleic acid inhibitor molecule can include a natural substituent, such as a hydroxyl or a phosphate group. In certain embodiments, a hydroxyl group is attached to the 5'-terminal end of the sense or antisense strand of the nucleic acid inhibitor molecule. In certain embodiments, a phosphate group is attached to the 5'-terminal end of the nucleic acid inhibitor molecule. Typically, the phosphate is added to a monomer prior to oligonucleotide synthesis. In other embodiments, 5'-phosphorylation is accomplished naturally after a nucleic acid inhibitor molecule is introduced into the cytosol, for example, by a cytosolic Clp1 kinase. In some embodiments, the 5'-terminal phosphate is a phosphate group, such as 5'-monophosphate [(HO)$_2$(O)P—O-5'], 5'-diphosphate [(HO)$_2$(O)P—O—P(HO)(O)—O-5'] or a 5'-triphosphate [(HO)$_2$(O)P—O—(HO)(O)P—O—P(HO)(O)—O-5'].

In certain embodiments one or two nucleotides of the optimized β-catenin nucleic acid inhibitor molecule are reversibly modified with a glutathione-sensitive moiety. Typically, the glutathione-sensitive moiety is located at the 2'-carbon of the sugar moiety and comprises a disulfide bridge or a sulfonyl group. In certain embodiment, the glutathione-sensitive moiety is compatible with phosphoramidite oligonucleotide synthesis methods, as described, for example, in International Application No. PCT/US2017/048239, which is hereby incorporated by reference in its entirety. In certain embodiments, more than two nucleotides of the optimized β-catenin nucleic acid inhibitor molecule are reversibly modified with a glutathione-sensitive moiety. In certain embodiments, most of the nucleotides are reversibly modified with a glutathione-sensitive moiety. In certain embodiments, all or substantially all the nucleotides of the optimized β-catenin nucleic acid inhibitor molecule are reversibly modified with a glutathione-sensitive moiety.

The at least one glutathione-sensitive moiety is typically located at the 5'- or 3'-terminal nucleotide of the passenger strand or the guide strand of a double-stranded nucleic acid inhibitor molecule. However, the at least one glutathione-sensitive moiety may be located at any nucleotide of interest in the optimized β-catenin nucleic acid inhibitor molecule.

Methods of Reducing β-Catenin Expression

The optimized nucleic acid inhibitor molecule, as described herein, can be used in methods of reducing β-catenin mRNA expression. Typically, the method of reducing β-catenin mRNA expression comprises administering the optimized nucleic acid inhibitor molecule, as described herein, to a sample or to a subject in need thereof in an amount sufficient to reduce expression of the β-catenin gene. The methods may be carried out in vitro or in vivo.

The level or activity of a β-catenin RNA can be determined by a suitable method now known in the art or that is later developed. It can be appreciated that the method used to measure a target RNA and/or the "expression" of a target gene can depend upon the nature of the target gene and its encoded RNA. For example, where the target β-catenin RNA sequence encodes a protein, the term "expression" can refer to a protein or the β-catenin RNA/transcript derived from the β-catenin gene (either genomic or of exogenous origin). In such instances the expression of the target β-catenin RNA can be determined by measuring the amount of β-catenin RNA/transcript directly or by measuring the amount of β-catenin protein. Protein can be measured in protein assays such as by staining or immunoblotting or, if the protein catalyzes a reaction that can be measured, by measuring reaction rates. All such methods are known in the art and can be used. Where target β-catenin RNA levels are to be measured, art-recognized methods for detecting RNA levels can be used (e.g., RT-PCR, Northern Blotting, etc.). In targeting β-catenin RNAs, measurement of the efficacy of the nucleic acid inhibitor molecule in reducing levels of β-catenin RNA or protein in a subject, tissue, in cells, either in vitro or in vivo, or in cell extracts can also be used to determine the extent of reduction of β-catenin-associated phenotypes (e.g., disease or disorders, e.g., cancer or tumor formation, growth, metastasis, spread, etc.), as disclosed, for example, in International Application No. PCT/US2017/022510. The above measurements can be made on cells, cell extracts, tissues, tissue extracts or other suitable source material.

Pharmaceutical Compositions

The present disclosure provides pharmaceutical compositions comprising a therapeutically effective amount of the optimized β-catenin nucleic acid inhibitor molecule, as described herein, and a pharmaceutically acceptable excipient.

These pharmaceutical compositions may be sterilized by conventional sterilization techniques, or may be sterile filtered. The resulting aqueous solutions may be packaged for use as is, or lyophilized, the lyophilized preparation being combined with a sterile aqueous excipient prior to administration. The pH of the preparations typically will be between 3 and 11, more preferably between 5 and 9 or between 6 and 8, and most preferably between 7 and 8, such as 7 to 7.5.

The pharmaceutical compositions of the present disclosure are applied for therapeutic use. Thus, one aspect of the disclosure provides a pharmaceutical composition, which may be used to treat a subject including, but not limited to, a human suffering from a disease or a condition by administering to said subject a therapeutically effective amount of a pharmaceutical composition of the present disclosure. Typically, the disease or condition is cancer, as described herein.

In certain embodiments, the present disclosure features the use of a therapeutically effective amount of a pharmaceutical composition as described herein for the manufacture of a medicament for treatment of a subject in need thereof. Typically, the subject has cancer, as described herein.

Pharmaceutically-Acceptable Excipients

The pharmaceutically-acceptable excipients useful in this disclosure are conventional. Remington's Pharmaceutical Sciences, by E. W. Martin, Mack Publishing Co., Easton, Pa., 15$^{th}$ Edition (1975), describes compositions and formulations suitable for pharmaceutical delivery of one or more therapeutic compositions. Some examples of materials which can serve as pharmaceutically-acceptable excipients include: sugars, such as lactose, glucose and sucrose; starches, such as corn starch and potato starch; cellulose and its derivatives, such as sodium carboxymethyl cellulose, ethyl cellulose and cellulose acetate; malt; gelatin; excipients, such as cocoa butter and suppository waxes; oils, such as peanut oil, cottonseed oil, safflower oil, sesame oil, olive oil, corn oil and soybean oil; buffering agents, such as magnesium hydroxide and aluminum hydroxide; (isotonic saline; Ringer's solution); ethyl alcohol; pH buffered solutions; polyols, such as glycerol, propylene glycol, polyethylene glycol, and the like; and other non-toxic compatible substances employed in pharmaceutical formulations.

Dosage Forms

The pharmaceutical compositions may be formulated with conventional excipients for any intended route of administration, which may be selected according to ordinary practice.

In one embodiment, the pharmaceutical composition contains the optimized β-catenin nucleic acid inhibitor molecule, as described herein, and is suitable for parenteral administration. The pharmaceutical composition optionally contains an immunotherapeutic agent, such as an antagonist of an inhibitory immune checkpoint molecule (e.g., one or more of an anti-CTLA-4, anti-PD-1, or anti-PD-L1 antibody) or an agonist of a co-stimulatory checkpoint molecule. Typically, the pharmaceutical compositions of the present disclosure that contain oligonucleotides are formulated in liquid form for parenteral administration, for example, by subcutaneous, intramuscular, intravenous or epidural injection.

Dosage forms suitable for parenteral administration typically include one or more suitable vehicles for parenteral administration including, by way of example, sterile aqueous solutions, saline, low molecular weight alcohols such as propylene glycol, polyethylene glycol, vegetable oils, gelatin, fatty acid esters such as ethyl oleate, and the like. The parenteral formulations may contain sugars, alcohols, antioxidants, buffers, bacteriostats, solutes which render the formulation isotonic with the blood of the intended recipient or suspending or thickening agents. Proper fluidity can be maintained, for example, by the use of surfactants. Liquid formulations can be lyophilized and stored for later use upon reconstitution with a sterile injectable solution.

The pharmaceutical compositions may also be formulated for other routes of administration including topical or transdermal administration, rectal or vaginal administration, ocular administration, nasal administration, buccal administration, or sublingual administration using well known techniques.

Delivery Agents

The optimized β-catenin nucleic acid inhibitor molecule, as described herein, may be admixed, encapsulated, conjugated or otherwise associated with other molecules, molecule structures or mixtures of compounds, including, for example, liposomes and lipids such as those disclosed in U.S. Pat. Nos. 6,815,432, 6,586,410, 6,858,225, 7,811,602, 7,244,448 and 8,158,601; polymeric materials such as those disclosed in U.S. Pat. Nos. 6,835,393, 7,374,778, 7,737,108, 7,718,193, 8,137,695 and U.S. Published Patent Application Nos. 2011/0143434, 2011/0129921, 2011/0123636, 2011/0143435, 2011/0142951, 2012/0021514, 2011/0281934, 2011/0286957 and 2008/0152661; capsids, capsoids, or receptor targeted molecules for assisting in uptake, distribution or absorption.

In certain embodiments, the optimized β-catenin nucleic acid inhibitor molecule is formulated in a lipid nanoparticle (LNP). Lipid-nucleic acid nanoparticles typically form spontaneously upon mixing lipids with nucleic acid to form a complex. Depending on the desired particle size distribution, the resultant nanoparticle mixture can be optionally extruded through a polycarbonate membrane (e.g., 100 nm cut-off) using, for example, a thermobarrel extruder, such as LIPEX® Extruder (Northern Lipids, Inc). To prepare a lipid nanoparticle for therapeutic use, it may desirable to remove solvent (e.g., ethanol) used to form the nanoparticle and/or exchange buffer, which can be accomplished by, for example, dialysis or tangential flow filtration. Methods of making lipid nanoparticles containing nucleic acid interference molecules are known in the art, as disclosed, for example in U.S. Published Patent Application Nos. 2015/0374842 and 2014/0107178.

In certain embodiments, the LNP comprises a core lipid component comprising a cationic liposome and a pegylated lipid. The LNP can further comprise one or more envelope lipids, such as a cationic lipid, a structural or neutral lipid, a sterol, a pegylated lipid, or mixtures thereof.

Figure 5:
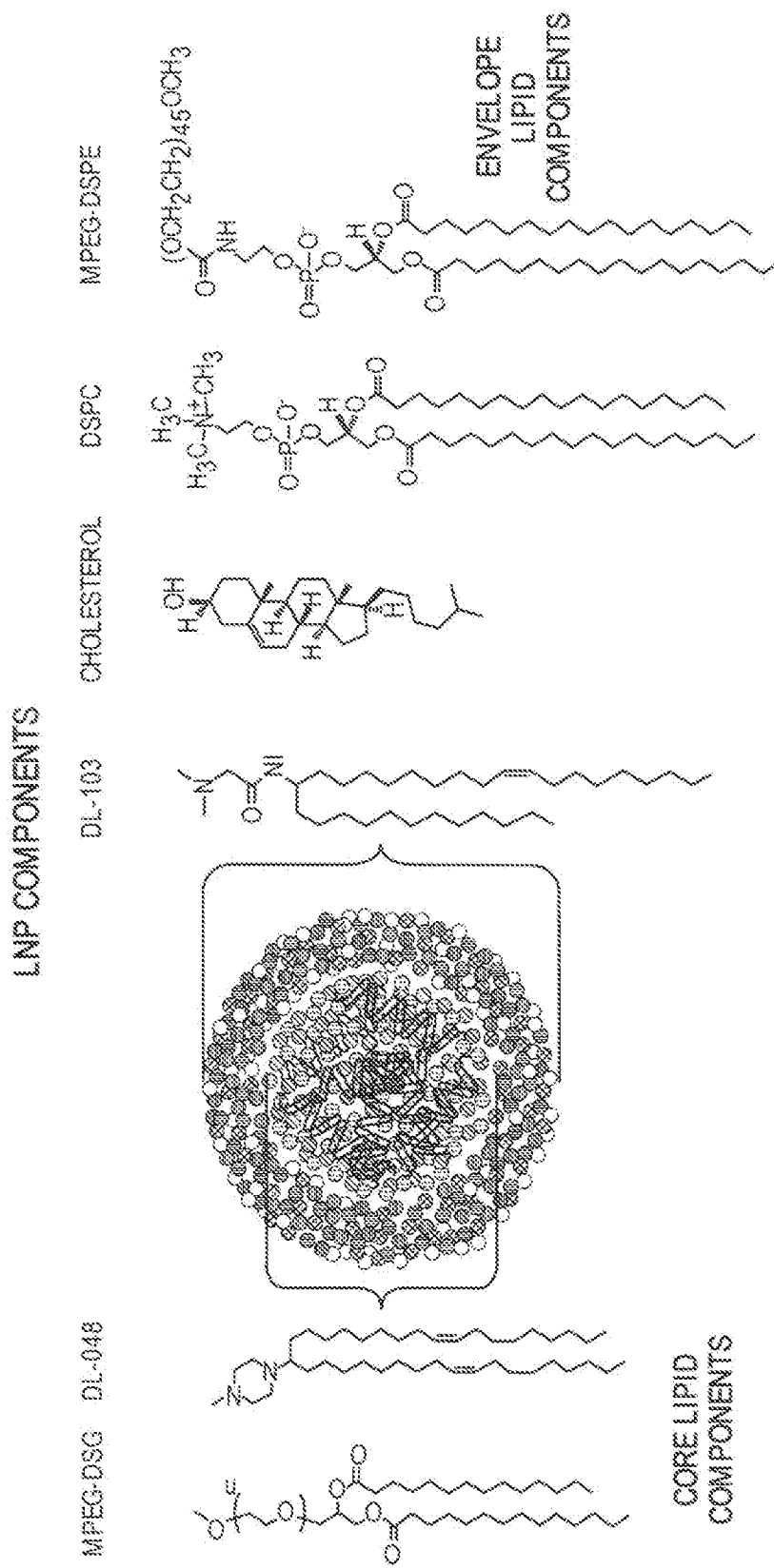
FIG. 5 shows one non-limiting embodiment of a lipid nanoparticle (LNP) that can be used to formulate the β-catenin nucleic acid inhibitor molecule. The LNP includes the following core lipids: DL-048 (cationic lipid) and DSG-MPEG (pegylated lipid), and the following envelope lipids: DL-103 (cationic lipid), DSPC, cholesterol, and DSPE-MPEG (pegylated lipid).

Cationic lipids for use in LNPs are known in the art, as discussed for example in U.S. Published Patent Application Nos. 2015/0374842 and 2014/0107178. Typically, the cationic lipid is a lipid having a net positive charge at physiological pH. In certain embodiments, the cationic liposome is DODMA, DOTMA, DL-048, or DL-103. In certain embodiments the structural or neutral lipid is DSPC, DPPC or DOPC. In certain embodiments, the sterol is cholesterol. In certain embodiments, the pegylated lipid is DMPE-PEG, DSPE-PEG, DSG-PEG, DMPE-PEG2K, DSPE-PEG2K, DSG-PEG2K, or DSG-MPEG. In one embodiment, the cationic lipid is DL-048, the pegylated lipid is DSG-MPEG and the one or more envelope lipids are DL-103, DSPC, cholesterol, and DSPE-MPEG. See e.g., FIG. 5, showing one non-limiting embodiment of a LNP that can used to formulate the optimized β-catenin nucleic acid inhibitor molecule.

In certain embodiments, the optimized β-catenin nucleic acid inhibitor molecule is covalently conjugated to a ligand that directs delivery of the oligonucleotide to a tissue of interest. Many such ligands have been explored. See, e.g., Winkler, Ther. Deliv. 4(7): 791-809 (2013). For example, the optimized β-catenin nucleic acid inhibitor molecule can be conjugated to one or more sugar ligand moieties (e.g., N-acetylgalactosamine (GalNAc)) to direct uptake of the oligonucleotide into the liver. See, e.g., U.S. Pat. Nos. 5,994,517; 5,574,142; WO 2016/100401. Typically, the optimized β-catenin nucleic acid inhibitor molecule is conjugated to three or four sugar ligand moieties. Other ligands that can be used include, but are not limited to, mannose-6-phosphate, cholesterol, folate, transferrin, and galactose (for other specific exemplary ligands see, e.g., WO 2012/089352).

Methods of Administration/Treatment

One embodiment is directed to a method of treating a β-catenin-associated disorder, comprising administering to a subject a pharmaceutical composition comprising a therapeutically effective amount of the optimized β-catenin nucleic acid inhibitor molecule, as described herein. In certain embodiments, the β-catenin-associated disorder is a cancer.

Non-limiting examples of such cancers include bilary tract cancer, bladder cancer, transitional cell carcinoma, urothelial carcinoma, brain cancer, gliomas, astrocytomas, breast carcinoma, metaplastic carcinoma, cervical cancer, cervical squamous cell carcinoma, rectal cancer, colorectal carcinoma, colon cancer, hereditary nonpolyposis colorectal cancer, colorectal adenocarcinomas, gastrointestinal stromal tumors (GISTs), endometrial carcinoma, endometrial stromal sarcomas, esophageal cancer, esophageal squamous cell carcinoma, esophageal adenocarcinoma, ocular melanoma, uveal melanoma, gallbladder carcinomas, gallbladder adenocarcinoma, renal cell carcinoma, clear cell renal cell carcinoma, transitional cell carcinoma, urothelial carcinomas, wilms tumor, leukemia, acute lymphocytic leukemia (ALL), acute myeloid leukemia (AML), chronic lymphocytic (CLL), chronic myeloid (CML), chronic myelomonocytic (CMML), liver cancer, liver carcinoma, hepatoma, hepatocellular carcinoma, cholangiocarcinoma, hepatoblastoma, Lung cancer, non-small cell lung cancer (NSCLC), mesothelioma, B-cell lymphomas, non-Hodgkin lymphoma, diffuse large B-cell lymphoma, Mantle cell lymphoma, T cell lymphomas, non-Hodgkin lymphoma, precursor T-lymphoblastic lymphoma/leukemia, peripheral T cell lymphomas, multiple myeloma, nasopharyngeal carcinoma (NPC), neuroblastoma, oropharyngeal cancer, oral cavity squamous cell carcinomas, osteosarcoma, ovarian carcinoma, pancreatic cancer, pancreatic ductal adenocarcinoma, pseudopapillary neoplasms, acinar cell carcinomas. Prostate cancer, prostate adenocarcinoma, skin cancer, melanoma, malignant melanoma, cutaneous melanoma, small intestine carcinomas, stomach cancer, gastric carcinoma, gastrointestinal stromal tumor (GIST), uterine cancer, or uterine sarcoma. In certain embodiments, the present disclosure features methods of treating liver cancer, liver carcinoma, hepatoma, hepatocellular carcinoma, cholangiocarcinoma and hepatoblastoma. In certain embodiments of the treatment methods, the cancer is colorectal cancer, hepatocellular carcinoma, or melanoma. In certain embodiments of the treatment methods, the cancer is a melanoma, a neuroblastoma, or a renal cancer.

In certain embodiments, the pharmaceutical compositions disclosed herein may be useful for the treatment or prevention of symptoms related to a Wnt activated disease or disorder, such as cancer. In other embodiments, the pharmaceutical compositions disclosed herein may be useful for the treatment or prevention of symptoms related to a non-Wnt activated disease or disorder, such as cancer.

In some embodiments, the cancer is associated with an activated Wnt/β-catenin pathway. In other embodiments, the cancer is a non-Wnt activated cancer. In certain embodiments, the subject has been identified as having a non-Wnt activated cancer before administering the optimized β-catenin nucleic acid inhibitor molecule. The subject may be identified as having a non-Wnt activated cancer using any method available to the skilled artisan. Typically, however, a sample from the subject is analyzed to determine if the subject has a non-Wnt activated cancer. In certain embodiments, the sample comprises tissue, cells, blood, or urine. In certain embodiments, the sample is analyzed for one or more biomarkers associated with an activated Wnt/β-catenin pathway, an inactive Wnt/β-catenin pathway and/or a non-T cell inflamed phenotype. Any appropriate biomarker can be analyzed, including, but not limited to nucleic acids (e.g., mRNA), proteins, and peptides using any suitable assay or technique. In certain embodiments, the biomarker is a gene mutation that is associated with an activated Wnt/β-catenin pathway, such as a mutation in a gene encoding β-catenin or APC or one or more other components involved in the Wnt/β-catenin pathway, such as, Axin, LEF, and ICAT.

In certain embodiments, the method of treating cancer further comprises administering a therapeutically effective amount of an immunotherapeutic agent. In some embodiments, the immunotherapeutic agent is as an antagonist of an inhibitory immune checkpoint molecule or an agonist of a co-stimulatory checkpoint molecule. In certain embodiments, the antagonist of an inhibitory immune checkpoint molecule is an anti-CTLA-4, anti-PD-1, anti-PD-L1 antibody, or a combination of thereof.

In certain embodiments, the cancer is resistant to immunotherapy, but the resistance to immunotherapy can be reversed by administering the immunotherapy in combination with a β-catenin nucleic acid inhibitor molecule, such as the optimized β-catenin nucleic acid inhibitor molecule described herein. Typically, cancer that is not responsive to immunotherapy is characterized by a non-T cell inflamed phenotype (also known as cold or non-inflamed tumors), with little to no infiltrating CD8+ T cells in the tumor microenvironment. Reducing β-catenin expression can convert a cold or non-inflamed tumor into a hot or inflamed tumor and potentiate the effect of immunotherapy, even in tumors that do not have an activated Wnt/β-catenin pathway. In other words, by combining a β-catenin inhibitor with immunotherapy, it is possible to treat cold or non-inflamed tumors that normally do not respond to immunotherapy. This combination therapy approach has been shown to potently inhibit tumor growth in vivo across a broad variety of cancers, including cancers with and without an activated Wnt/β-catenin pathway, as described for example, in U.S. Provisional Application No. 62/477,783, which is hereby incorporated by reference in its entirety. In certain embodiments, the cancer is a non-Wnt activated cancer. In certain embodiments, the cancer is a Wnt activated cancer.

In some embodiments, the present disclosure provides a method of potentiating an in vivo immune response against a cancer, comprising administering to a subject having cancer the optimized β-catenin nucleic acid inhibitor molecule, as described herein, in an amount sufficient to potentiate the therapeutic effect of immunotherapy against the cancer or otherwise render the cancer susceptible to the immunotherapy. Typically, prior to administering the optimized β-catenin nucleic acid inhibitor molecule, the cancer is associated with a non-T cell inflamed phenotype that is resistant to immunotherapy and administering the modified β-catenin nucleic acid inhibitor molecule converts the non-T cell inflamed phenotype into a T cell-inflamed phenotype, such that the cancer becomes responsive to immunotherapy. In certain embodiments, the cancer that is resistant to immunotherapy is a Wnt activated cancer. In other embodiments, the cancer that is resistant to immunotherapy is a non-Wnt activated cancer.

Dosing and Schedule

Typically, the optimized β-catenin nucleic acid inhibitor molecule is administered parenterally (such as via intravenous, intramuscular, or subcutaneous administration). In other embodiments, the pharmaceutical composition is delivered via local administration or systemic administration. However, the pharmaceutical compositions disclosed herein may also be administered by any method known in the art, including, for example, buccal, sublingual, rectal, vaginal, intraurethral, topical, intraocular, intranasal, and/or intraauricular, which administration may include tablets, capsules, granules, aqueous suspensions, gels, sprays, suppositories, salves, ointments, or the like.

In certain embodiments, the optimized β-catenin nucleic acid inhibitor molecule is administered at a dosage of 20 micrograms to 10 milligrams per kilogram body weight of the recipient per day, 100 micrograms to 5 milligrams per kilogram, 0.25 milligrams to 5.0 milligrams per kilogram, or 0.5 to 3.0 milligrams per kilogram. Typically, the optimized β-catenin nucleic acid inhibitor molecule is administered at a dosage of about 0.25 to 2.0 milligrams per kilogram body weight of the recipient per day.

A pharmaceutical composition of the instant disclosure may be administered every day, or intermittently. For example, intermittent administration of the optimized β-catenin nucleic acid inhibitor molecule may be administration one to six days per week, one to six days per month, once weekly, once every other week, once monthly, once every other month, or once or twice per year or divided into multiple yearly, monthly, weekly, or daily doses. Typically, the optimized β-catenin nucleic acid inhibitor molecule is administered every week or every two weeks. In some embodiments, intermittent dosing may mean administration in cycles with the initial optimized β-catenin nucleic acid inhibitor molecule or immunotherapeutic agent administration followed by a rest period with no administration for up to one week, up to one month, up to two months, up to three months or up to six months or more) or it may mean administration on alternate days, weeks, months or years.

When combined with an immunotherapeutic agent, the β-catenin nucleic acid inhibitor molecule is typically administered separately from, and on a different schedule than, the immunotherapeutic agent. Pharmaceutical compositions containing the immunotherapeutic agent are typically administered intravenously. For example, when used as a single agent, ipilimumab (anti-CTLA-4 antibody) is administered intravenously over 90 minutes at a recommended dose of 3 mg/kg every 3 weeks for a total of 4 doses. Similarly, when used as a single agent, nivolumab (anti-PD-1 antibody), is administered intravenously at a recommended dose of 240 mg (or 3 mg/kg) over 60 minutes every 2 weeks. When nivolumab is administered in combination with ipilimumab, the recommended dose of nivolumab is 1 mg/kg administered intravenously over 60 minutes, followed by ipilimumab on the same day at a recommended dose of 3 mg/kg every 3 weeks for a total of 4 doses, and then nivolumab at a recommended dose of 240 mg every 2 weeks.

In certain embodiments, the optimized β-catenin nucleic acid inhibitor molecule is administered before the immunotherapeutic agent. In certain embodiments, the optimized β-catenin nucleic acid inhibitor molecule is administered after the immunotherapeutic agent. In certain embodiments, the patient has been previously treated with the therapeutic agent before beginning treatment with the optimized β-catenin nucleic acid inhibitor molecule. The therapeutically effective amount of the optimized β-catenin nucleic acid inhibitor molecule or immunotherapeutic agent may depend on the route of administration and the physical characteristics of the patient, such as the size and weight of the subject, the extent of the disease progression or penetration, the age, health, and sex of the subject and can be adjusted as necessary depending on these and other factors.

EXAMPLES

Example 1: Modified Beta-Catenin (BCAT) Nucleic Acid Inhibitor Molecules

Several nucleic acid inhibitor molecules that target the beta-catenin gene were made with different modification patterns to assess how the modification patterns might affect different properties of the molecules, such as immunogenicity, modulation of β-catenin mRNA expression, and/or Ago2 binding. To this end, alternative structural classes of double-stranded nucleic acid inhibitor molecules were tested, including earlier generation, "non-extended" molecules having a blunt end at the right-hand side of the molecule (i.e., at 3' terminus of the passenger strand and 5' terminus of the guide strand), as shown in FIG. 1A, and next generation "extended" molecules having a guide strand with a single-stranded extension of 10 nucleotides at its 5' terminus, as shown in FIG. 2A. In FIGS. 1A and 2A, unshaded nucleotide contain a ribose, lightly shaded nucleotides contain a ribose with a 2'-OMe modification, the darker shaded nucleotides contain a ribose with a 2'-F modification, and nucleotides surrounded by a bolded box contain a deoxyribose.

Non-Extended Nucleic Acid Inhibitor Molecules

Three non-extended nucleic acid inhibitor molecules were constructed: NonExtend M1 (NEX M1), NonExtend M2 (NEX M2), and NonExtend M3 (NEX M3). NEX M1 has passenger and guide strands consisting of 25 and 27 base pairs, respectively. Together, the passenger and guide strands form a duplex region consisting of 25 base pairs with a two-base pair, single-stranded, overhang at the 3' end of the guide strand. A number of 2'-OMe modifications (lightly shaded boxes) were incorporated into the passenger and guide strands of NEX M1. The last two nucleotides at the 3'-terminus of the passenger strand contain a deoxyribose. FIG. 1A.

Several 2'-F modifications (darker shaded bases) were introduced into NEX M1 to generate NEX M2. Except for the changes in the modification pattern of the bases, the nucleotide sequences of the passenger and guide strands of NEX M2 are identical to those of NEX M1. FIG. 1A. Next, NonExtend M3 (NEX M3) was generated by adding four additional 2'-F modifications to NEX M2. The passenger and guide strands of NEX M2 and NEX M3 have the same nucleotide sequence, 25 base pair duplex region, and 3' overhang as in NEX M1, the only differences being the 2'-F modification pattern.

Converting NEX M1 into an NEX M2 or NEX M3 structure did not affect intrinsic potency as demonstrated by the IC50 values of those constructs in cells (0.9 pM, 0.8 pM, and 0.8 pM, respectively), as shown in FIG. 1A. To determine if the modification patterns in these sequences affect immunogenicity of the double-stranded nucleic acid constructs, the interferon response was measured after treating human PBMCs with NEX M1, NEX M2, and NEX M3. PBMCs were isolated from human blood samples from different donors by gradient centrifugation using Ficoll-Histophaque. Isolated PBMCs were treated with the double-stranded nucleic acid constructs mixed with DOTAP (liposomal transfection reagent and immune adjuvant) for different period of times and IF1T1 induction (an interferon induced gene) was monitored by solid state cDNA synthesis followed by qPCR. An unmodified double-stranded nucleic acid inhibitor molecule (21 nucleotides in length) that targets the Bcl2 gene was mixed with DOTAP (Avanti Polar Lipids, Alabaster, Ala.) and used as a reference in this experiment. NEX M1 demonstrated significant elevation of IF1T1 while NEX M2 showed moderate elevation. NEX M3, on the other hand, was very quiet compared to NEX M1 and NEX M2, suggesting that the specific combination of 2'-OMe and 2'-F modifications in NEX M3 substantially diminished the interferon response induced by NEX M3 in human PBMCs (FIG. 1B).

Extended Nucleic Acid Inhibitor Molecules

Next generation, extended, double-stranded nucleic acid constructs were generated by adding a 10-base pair single-stranded overhang at the 5'-end of the guide strand. This 10-base pair single-stranded overhang also includes additional 2'-OMe and 2'-F modifications. An extra C/G base pair was also incorporated at the right-hand side of the duplex before the 10-base pair single-stranded overhang, as shown in FIG. 2A. Incorporation of the extra C/G base pair and 10-base pair extension into the NEX M1, NEX M2 and NEX M3 constructs produced the EX M1, EX M2 and EX M3 constructs, respectively, as shown in FIG. 2A.

Intrinsic potency of EX M1 was slightly affected but the incorporation did not substantially affect the potency of EX M2 and EX M3 as shown by the IC50 values in FIG. 2A. The interferon response of EX M1, EX M2, and EX M3 in human PBMCs was measured as described above in Example 2. A trend towards decreased immune stimulation was observed from EX M1 to EX M2 to EX M3 (FIG. 2B), similar to the trend observed in the nonextended constructs, suggesting that the specific combination of 2'-OMe and 2'-F modifications into the extended, double-stranded nucleic acid constructs reduces interferon responses.

Example 2: Further Evaluation of Selected BCAT Constructs

The nonextended construct with the smallest interferon response (NEX M3) was compared to the extended construct with the smallest interferon response (EX M3) for interferon response (as measured by IF1T1 induction as previously described) in human PBMCs from 4 different donors. NEX M1 was also included in the comparison.

Figure 3A:
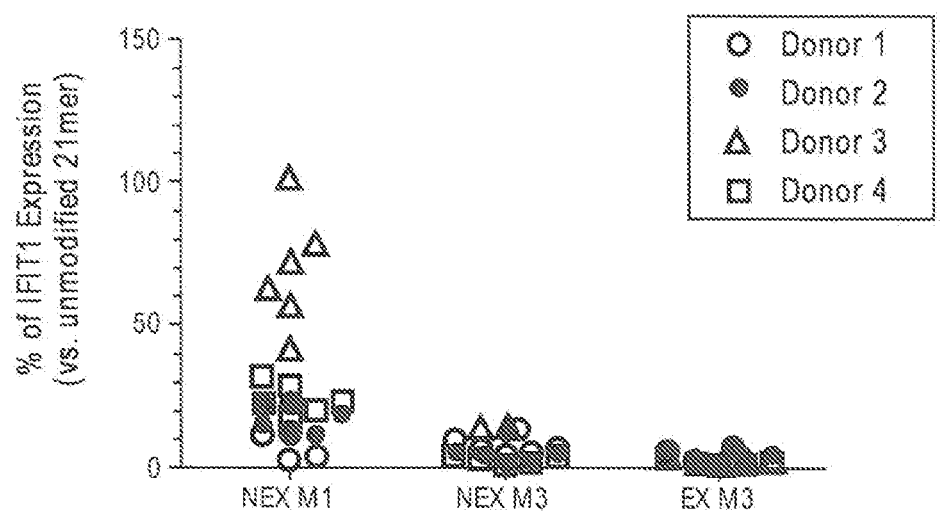
FIG. 3A shows the results from an assay in which relative immunogenicity was assessed by measuring the impact on interferon levels for NEX M1, NEX M3, and EX M3 when mixed with human PBMCs from four different donors. NEX M3 and EX M3 showed little or no interferon response for all four donors, whereas NEX M1 showed a modest interferon response for Donors 1, 2, and 4 and a substantial interferon response for Donor 3 (hypersensitive).

NEX M3 and EX M3 showed essentially no interferon response in all 4 donor PBMCs, whereas NEX M1 showed a modest interferon response when treated with PMBCs from Donors 1, 2, and 4 and a substantial interferon response when treated with PMBCs from the hypersensitive Donor 3 (FIG. 3A). Thus, the specific combination of 2'-OMe and 2'-F modifications in NEX M3 and EX M3 successfully decreased the interferon response caused by these nucleic acid constructs in human PBMCs.

Example 3: Beta-Catenin (CTNNB1) mRNA Knockdown in Tumors

Figure 3B:
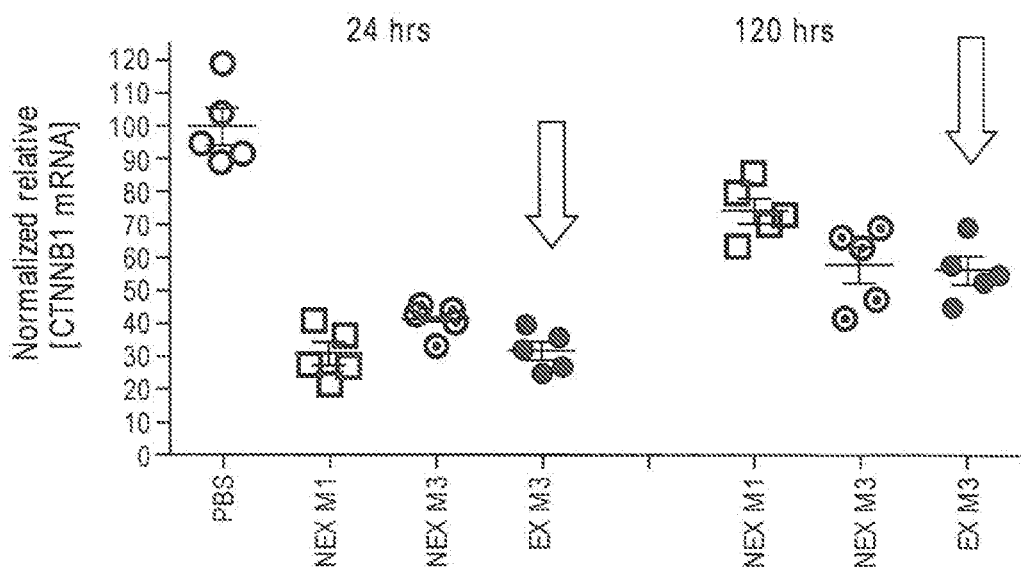
FIG. 3B shows the amount of beta-catenin mRNA knockdown ("potency") in LS411N tumors at different time points (24 and 120 hours post-treatment) obtained from mice treated with NEX M1, NEX M3, and EX M3. At 24 hours, EX M3 demonstrated slightly better potency when compared to EX M2 and NEX M3 and similar potency compared to NEX M1. At 120 hours after treatment, EX M3 showed an improved potency as compared to NEX M1.

To see how the modification patterns influence the target engagement in tumors, the NEX M1, NEX M3, and EX M3 constructs were formulated in EnCore lipid nanoparticles (LNP) and tested for activity. The nucleic acid formulated LNPs were evaluated at different time points in tumor bearing mice. To generate tumors, 6-8 week old Hsd: Athymic Nude-Foxn1$^{nu}$ mice were injected subcutaneously with LS411N ($5\times10^6$ cells) under the right shoulder. Tumor volume was measured every 2-3 days to monitor tumor growth. When the tumors reached 200-250 mm$^3$, the animals were randomized and assigned to different cohorts and injected with LNPs carrying different double-stranded nucleic acid inhibitor molecule constructs as listed in FIG. 3B. LNP was administered intravenously via lateral tail vein at a total volume of 10 ml/kg. Tumor samples were collected at 24 and 120 hours after the dose and subjected to mRNA analysis. EX M3 demonstrated slightly better potency when compared to NEX M3 but had similar potency to NEX M1 24 hours after dosing (FIG. 3B). However, EX M3 showed improved potency 120 hours after dosing compared to NEX M1 but had similar potency to NEX M3. Based on the interferon response and potency and duration effect, EX M3 was selected for further characterization.

Example 4: Comparing NEX M1 to EX M3

Figure 4A:
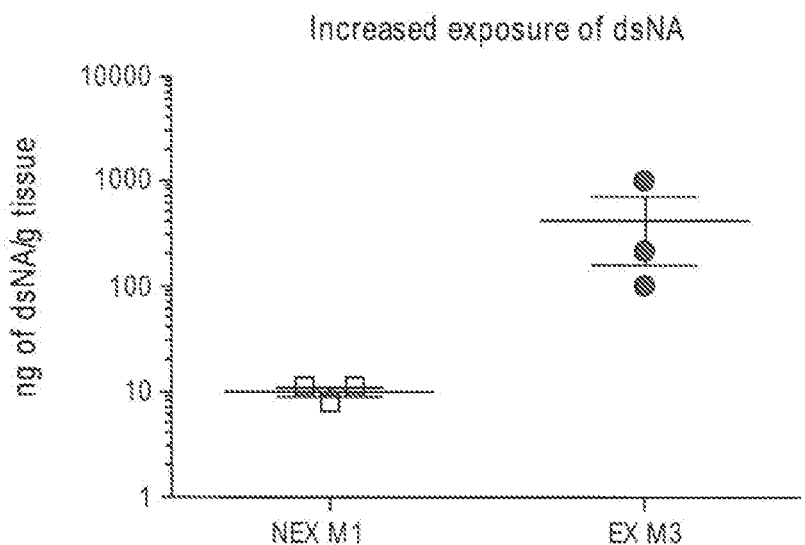
FIGS. 4A-D show graphs or images of results from various assays comparing the NEX M1 and EX M3 constructs.
Figure 4B:
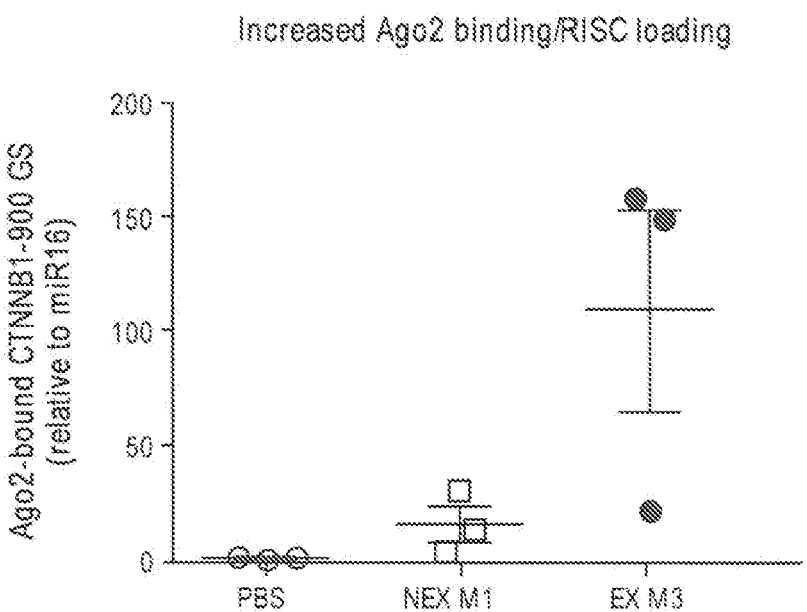

The properties of EX M3 were further evaluated by comparing it with the earlier generation NEX M1. To investigate possible mechanisms for this increased potency, the exposure levels and levels of Ago2 binding (RISC incorporation) of each construct in the tumor homogenates were also compared. EX M3 (antisense strand) was detected in tumor tissue on day 16 post tumor transplant at approximately 5-100× higher levels than NEX M1 (FIG. 4A) after treating the LS411N tumor bearing mice at 3 mg/kg for 3 days (days 14, 15, and 16 post tumor transplant). In addition, on day 16 post tumor transplant, EX M3 (antisense strand) showed approximately 5-10× more Ago2 binding/RISC loading than NEX M1 (FIG. 4B) after treating the LS411N tumor bearing mice at 3 mg/kg for 3 days (days 14, 15, and 16 post tumor transplant), demonstrating that EX M3 appears to be more stable and active than the earlier generation NEX M1.

Figure 4C:
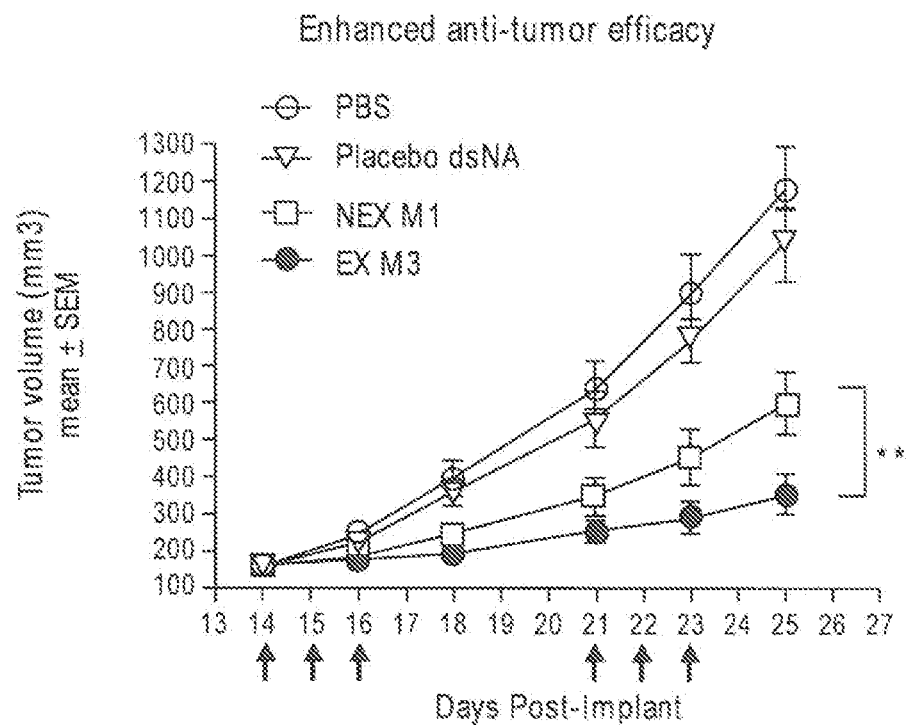
Figure 4D:
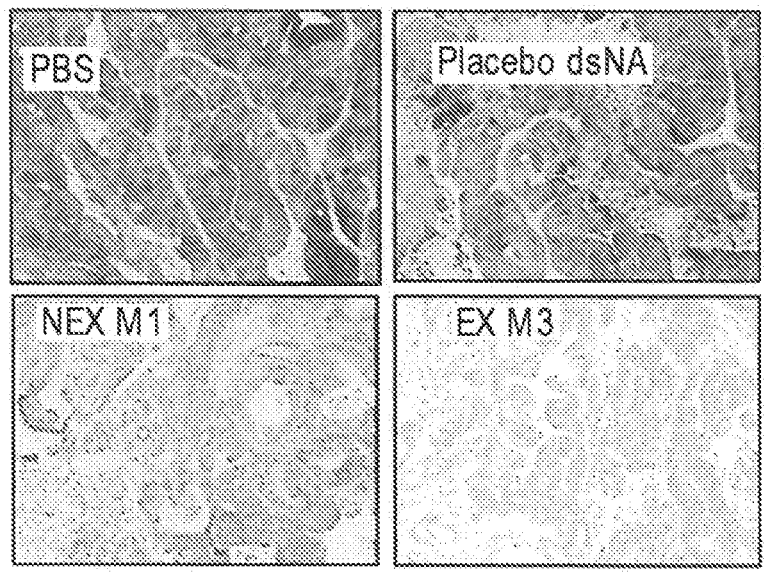

To see if the improved properties of EX M3 translated into anti-tumor efficacy, SW403 tumor bearing mice were treated with LNP-formulated NEX M1 or EX M3 along with Placebo and PBS at qdx3, 3 mg/kg dose levels (2 cycles). After two weekly dosing cycles (qdx3, 3 mg/kg), NEX M1 induced tumor growth inhibition of about 55% relative to vehicle-treated animals, whereas the EX M3 induced over 80% growth inhibition (FIG. 4C). At the end of the study, the tumors were also stained for beta-catenin protein. As shown in FIG. 4D, there was a substantial decrease in beta-catenin protein levels from the EX M3-treated tumors compared to NEX M1-treated tumors, suggesting that the improved potency and duration caused by the EX M3 construct led to increased anti-tumor efficacy in tumors treated with EX M3.

Example 5: Inhibiting β-Catenin Wnt Active 4T1 Tumors

Balb/C mice were implanted with 4T1 tumors. At six days post 4T1 tumor cell implantation, with the average tumor size of 150-200 mm$^3$, mice were sorted into two groups and were treated with either placebo or EX M3 at 3 mg/kg on days 6 and 7 and days 12 and 13 post-implant, as shown in FIG. 7A. 48 hours after the last dose, tumors were collected and assayed by immunohistochemistry for β-catenin, CD8 and IDO1 protein levels. As shown in FIG. 7B, EX M3 treatment decreased β-catenin levels and increased CD8 levels but did not reduce the IDO1 levels significantly after two rounds of treatment.

In another study, 4T1 tumor cells were implanted in Balb/C mice and 4 days post-implant, the mice were randomized into two groups and treated with placebo or EX M3. Mice were administered two doses of placebo or EX M3 at 3 mg/kg on days 4 and 5, as shown in FIG. 7C. This combination dosing cycle was then repeated on days 9 and 10. Tumor growth was monitored by measuring the tumor sizes over the course of the treatment period. Treating mice with EX M3 alone resulted in tumor growth inhibition of about 40%. FIG. 7C.

Figure 8A:
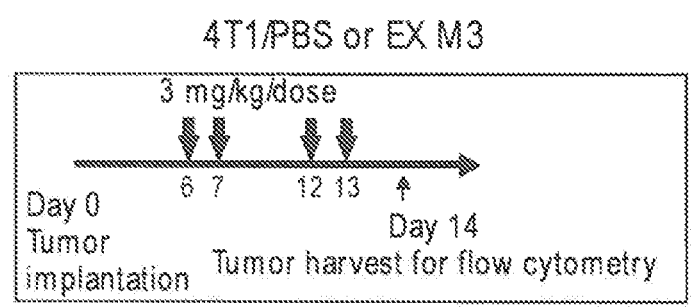
FIG. 8A shows the treatment schedule for Balb/C mice that were implanted with 4T1 tumors and treated with PBS or EX M3, as described in Example 5.
Figure 8B:
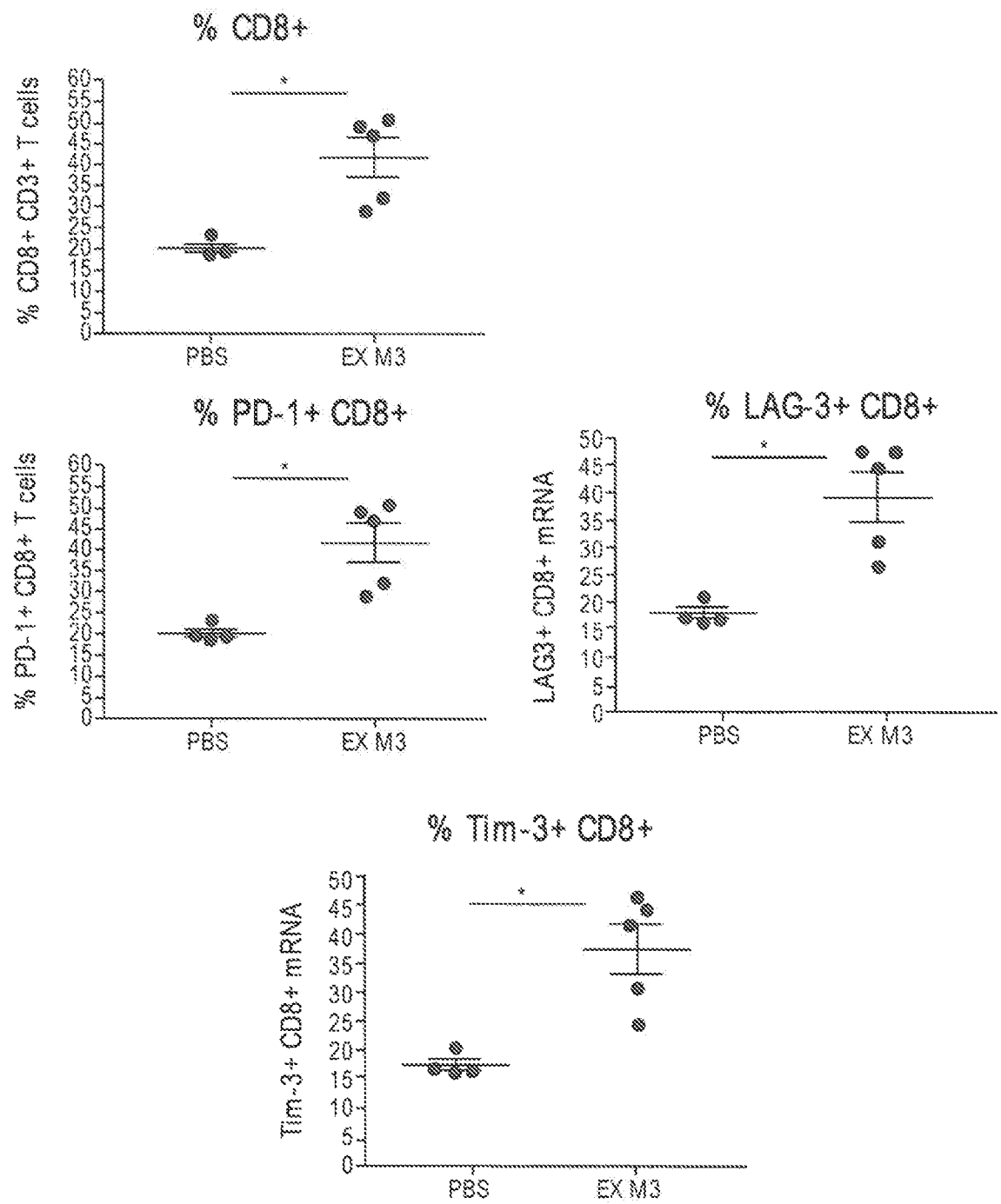
FIG. 8B shows by flow cytometry analysis that EX M3 treatment of 4T1 tumors increases CD8+ T cells, increases multiple checkpoint molecules (PD-1, LAG-3+, and Tim-3+), and increases regulator T cells (Tregs) but does not significantly alter the number of myeloid derived suppressor cells (MDSC) in the tumor microenvironment.
Figure 8B:
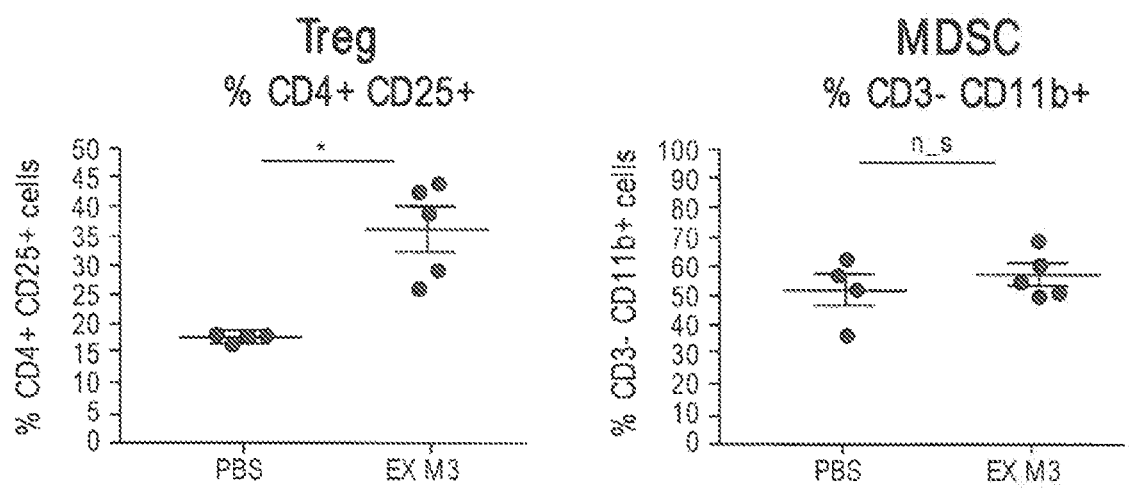

In another similar study, mice bearing 4T1 tumors were treated with PBS or EX M3 at 3 mg/kg on days 6 and 7 and days 12 and 13 post-implant, as shown in FIG. 8A. Tumors were collected 24 hours after the last dose and subjected to flow cytometry to measure surface markers on single-cell suspensions prepared from the extracted tumors. While the PBS control had no significant effect on the tumor immune microenvironment, EX M3 treatment resulted in significant increases in cytotoxic T-cells (CD8), and multiple checkpoints (PD-1, LAG-3 and Tim-3). FIG. 8B. EX M3 treatment significantly increased Regulatory T cells (Tregs), which play an important role in regulating or suppressing other cells of the immune system. FIG. 8B. No effect was observed on the immunosuppressive MDSC cells. FIG. 8B.

Example 6: Inhibiting IDO1 in Wnt Active 4T1 Tumors

Another efficacy study was performed in 4T1 tumors with the IDO1 inhibitor, Epacadostat (IDOi). 4T1 tumor bearing mice were randomized into two groups and treated orally with vehicle or IDOi twice daily at 100 mg/kg per dose on days 6 and 8 post-implant, as shown in FIG. 9A. Tumors were collected 48 hours after the last dose and were subjected to immunohistochemistry to look at β-catenin, CD8 and IDO1 levels. IDOi at 100 mg/kg reduced the IDO1 levels almost completely. FIG. 9B. β-catenin levels were modestly decreased and CD8 levels were slightly increased. FIG. 9B. In a related study, mice bearing 4T1 tumors were administered placebo or IDOi twice daily at 100 mg/kg per day on days 6 and 8 post-implant, as shown in FIG. 9C. Tumor growth was monitored by measuring the tumor sizes over the course of the treatment period. Treating mice with IDOi alone led to tumor growth inhibition, suggesting that, in addition to β-catenin, the 4T1 tumors also depend on IDO1 for tumor growth. FIG. 9C.

Figure 10A:
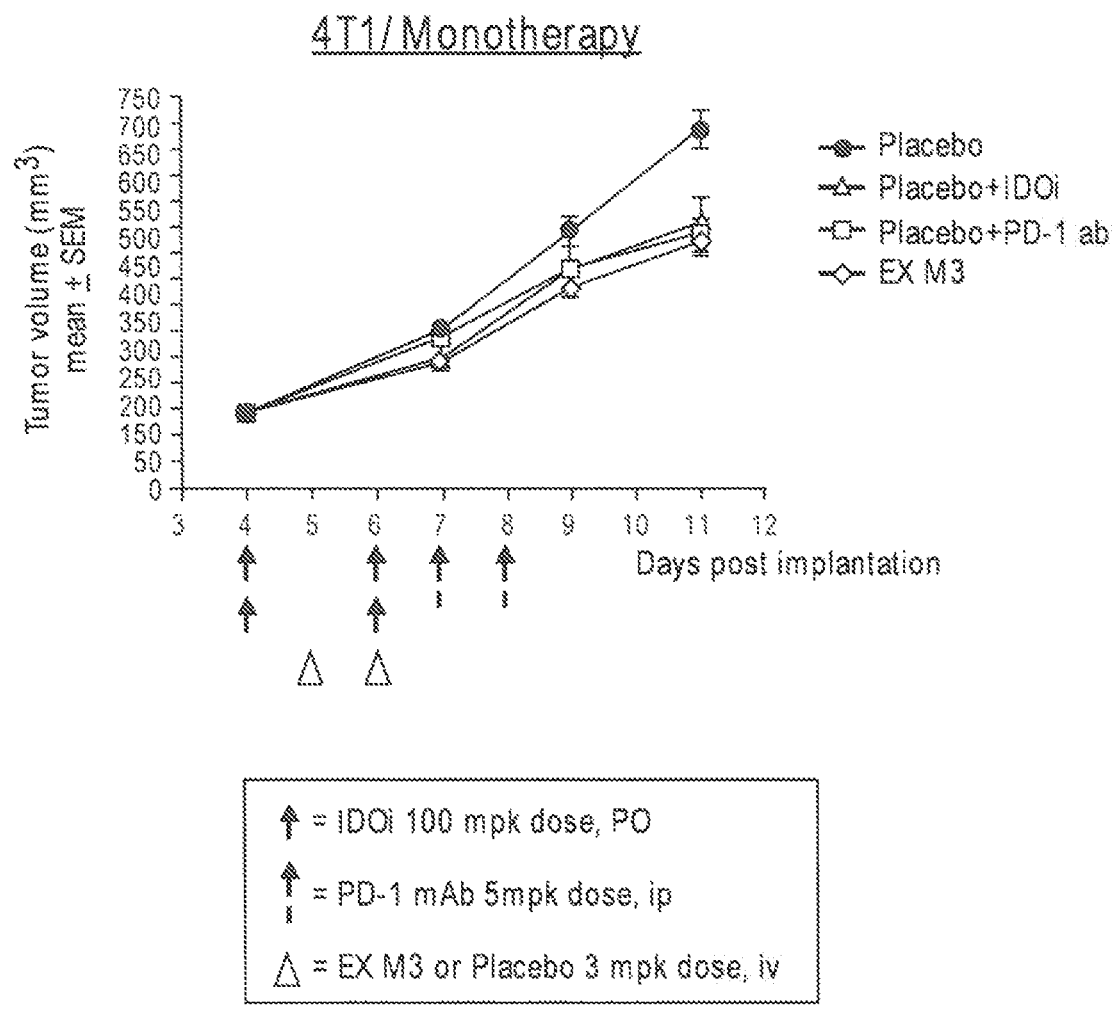
FIGS. 10A-C show the efficacy of IDOi (epacadostat), an anti-PD-1 antibody (PD-1), and EX M3 administered as single agents (FIG. 10A), combinations of two agents (FIG. 10B), or combinations of three agents (FIG. 10C) in Balb/C mice implanted with 4T1 tumors, with the combination of all three agents showing tumor regression, as described in Example 7.
Figure 10B:
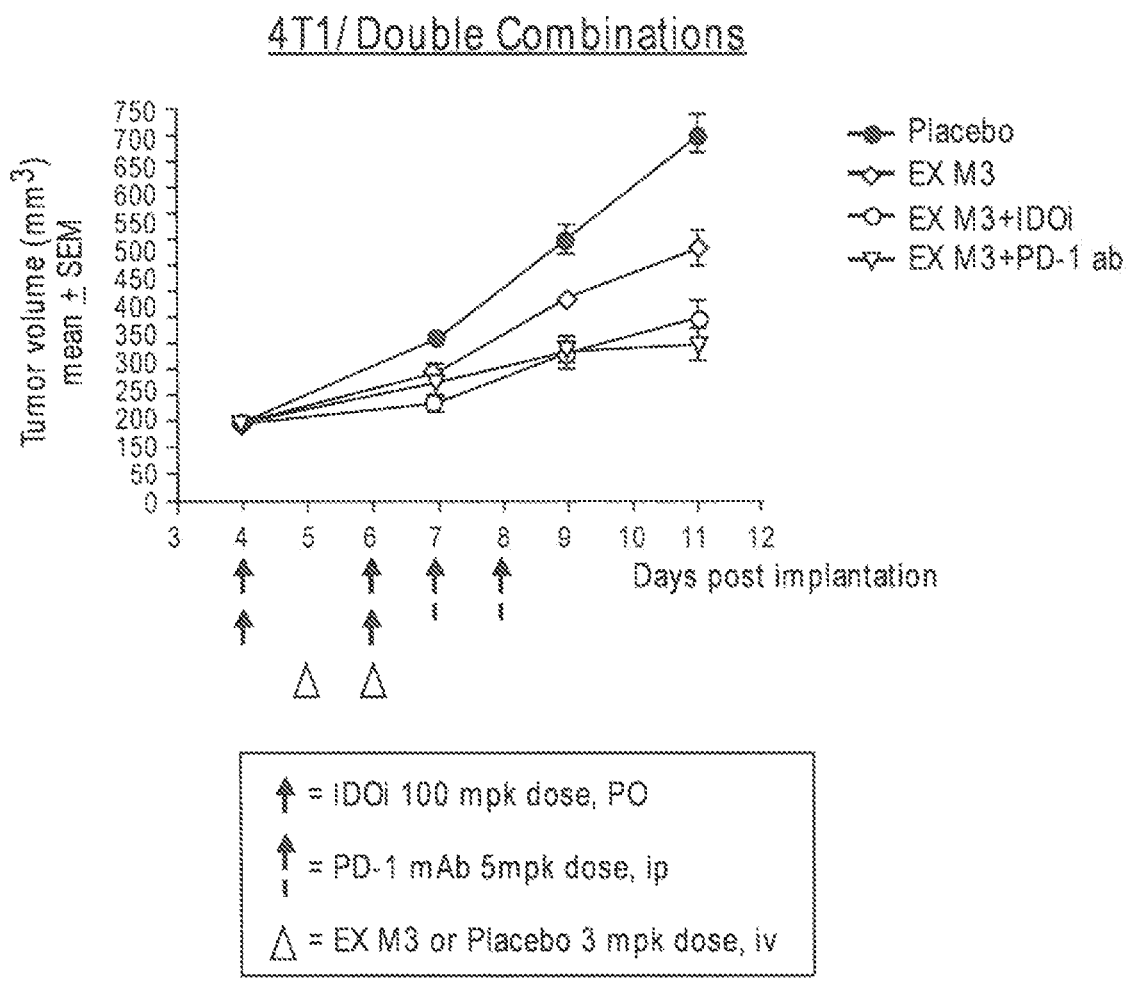
Figure 10C:
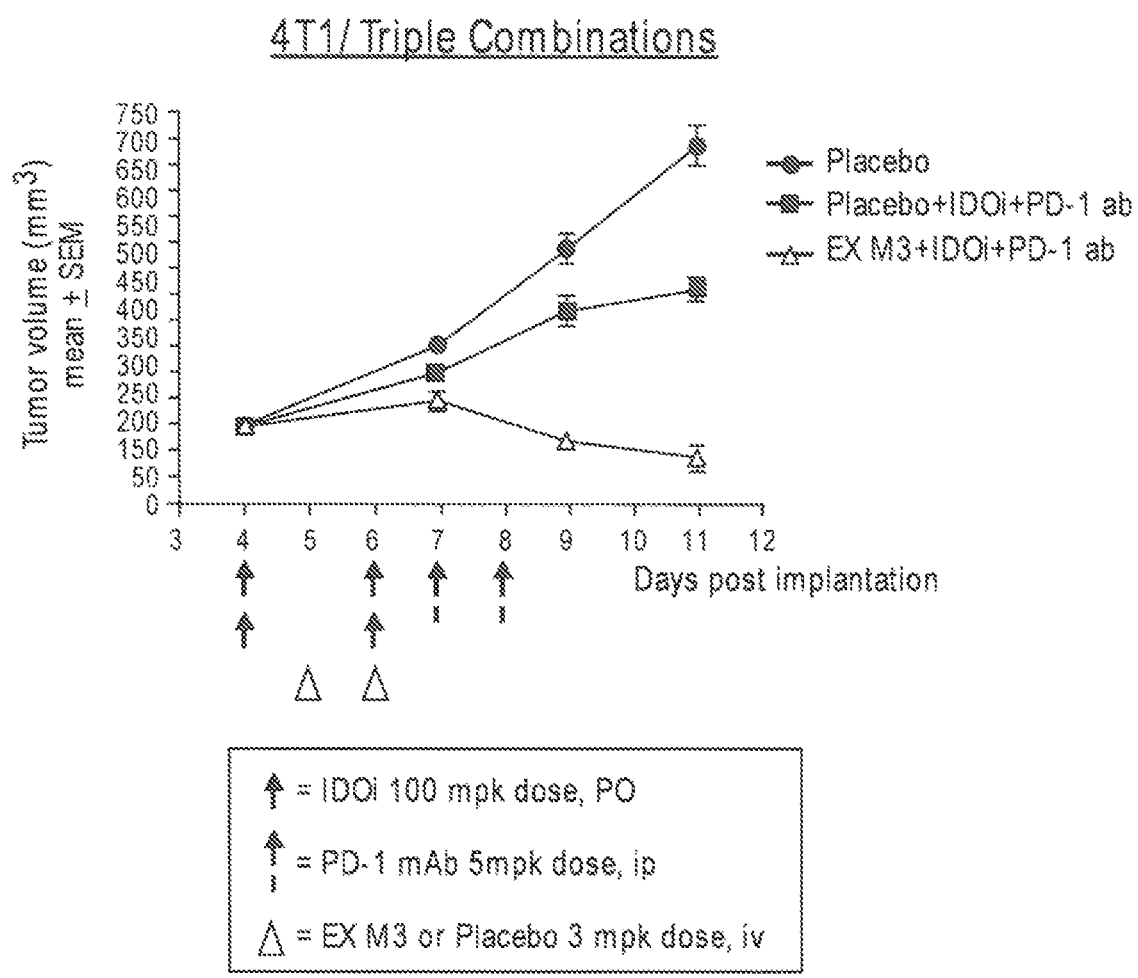

Example 7: Inhibiting IDO1 in Wnt Active 4T1 Tumors in Combination with β-Catenin Inhibition and/or a Checkpoint Inhibitor Next, combination therapy in 4T1 tumors with EX M3 and IDOi or EX M3 and a checkpoint inhibitor (anti PD-1 antibody) or triple combination therapy with EX M3, IDO1, and an anti-PD-1 antibody was assessed. 4T1 tumor bearing mice were sorted into 8 groups (n=5) and pre-treated twice daily with IDOi (orally at 100 mg/kg per dose) on days 4 and 6 post-implant and EX M3 or placebo (iv at 3 mg/kg per dose) on days 5 and 6 post-implant, followed by anti-PD-1 antibody (ip at 5 mg/kg per dose) on days 7 and 8 post-implant, as shown in FIG. 10C. Mice also received EX M3, IDOi and PD-1 antibody as single agents (FIG. 10A) and combinations of two agents (FIG. 10B). Mice receiving EX M3, IDOi, or anti-PD1 antibody as monotherapy showed modest anti-tumor efficacy. FIG. 10A. The mice that received combination therapy with EX M3 and anti-PD-1 antibody or EX M3 and IDOi demonstrated tumor stasis, reducing the rate of tumor growth. FIG. 10B. Remarkably, mice that were treated with all three agents (EX M3, IDOi and anti-PD-1 antibody) demonstrated tumor regression, as shown in FIG. 10C, with pronounced reduction of the tumor volume starting after administration of all three agents. Notably, as shown in FIG. 10C, the anti-tumor effect of the triple combination of EX M3, epacadostat (IDOi), and the anti-PD-1 antibody was markedly superior to the effect observed with the double combination of epacadostat (IDOi) and the anti-PD-1, which is currently being evaluated in Phase III studies.

Figure 11A:
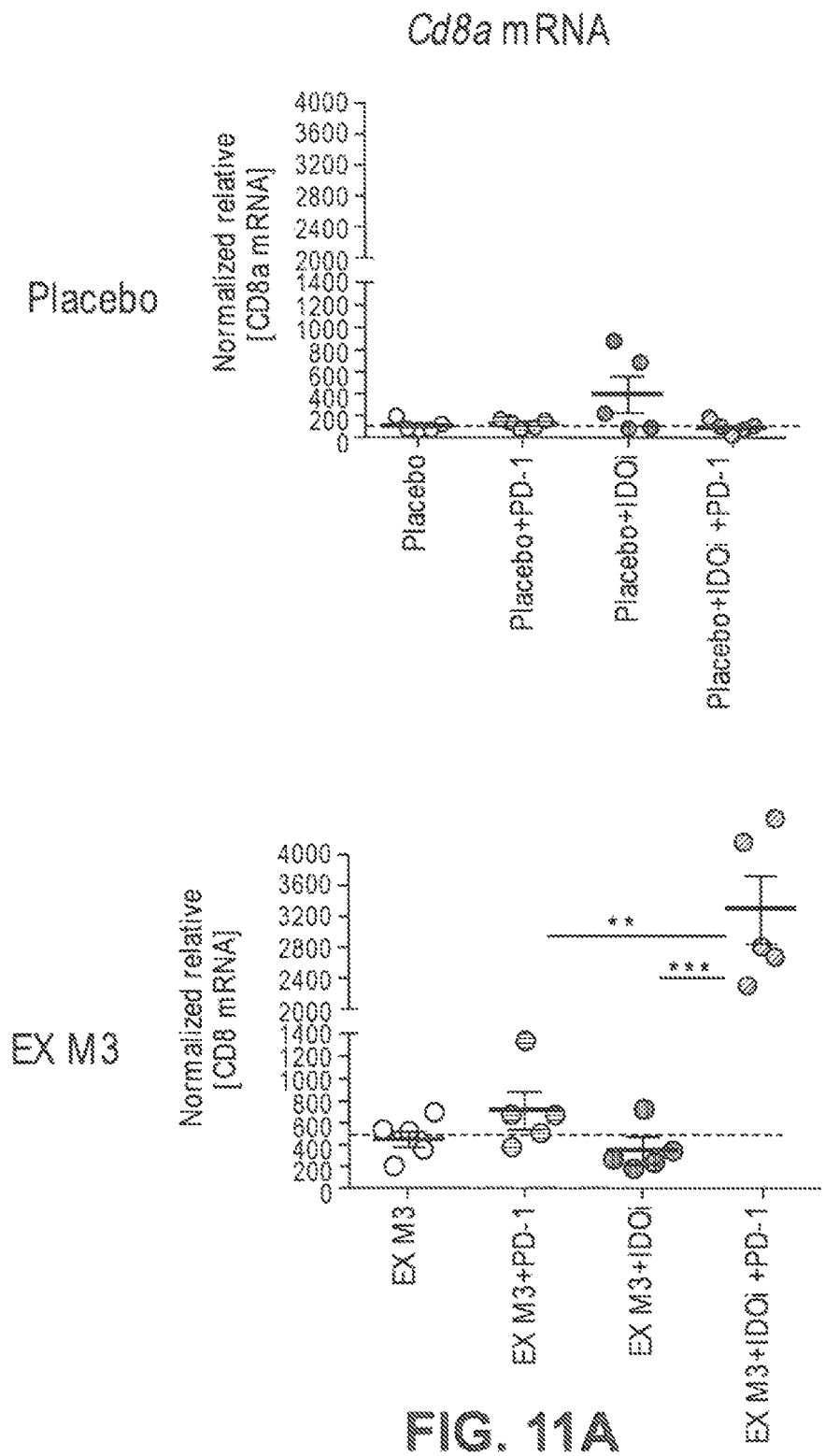
FIGS. 11A-B show the mRNA levels of CD8 (FIG. 11A) and Foxp3 (FIG. 11B) in 4T1 tumors treated with IDOi, anti-PD-1 antibody and/or EX M3 and demonstrates that only the combination of all three agents significantly increased CD8 mRNA levels and significantly decreased Foxp3 mRNA levels.
Figure 11B:
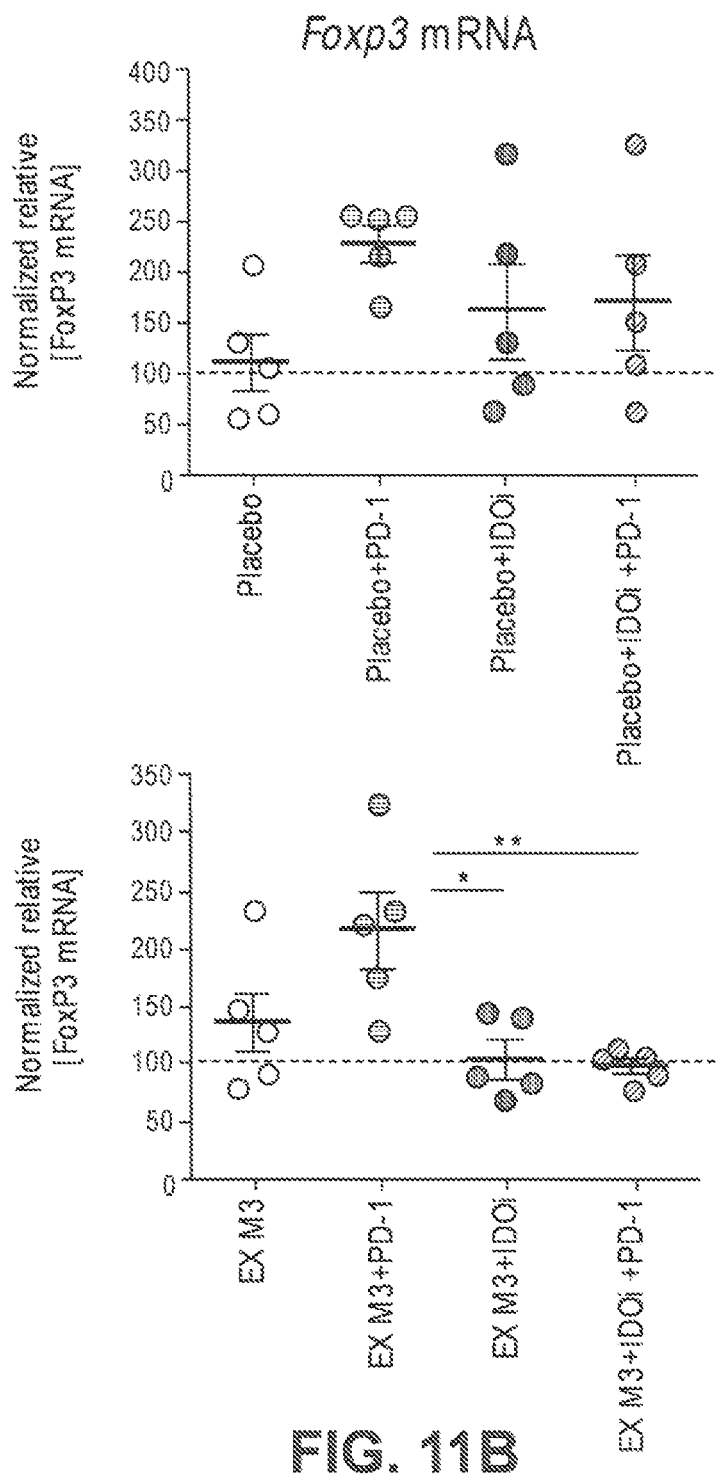

At the end of the study (72 hours after the last anti-PD-1 antibody treatment), tumors were collected and subjected to qPCR to analyze certain T cell markers. There was a substantial increase in CD8 mRNA observed in the mice that received the triple combination treatment as compared to the other groups. FIG. 11A. FoxP3 is a marker for immunosuppressive T cells called Tregs. Foxp3 mRNA levels were increased when the anti-PD-1 antibody was added to either placebo or EX M3 treatment. FIG. 11B. These levels were returned to background levels with the addition of IDOi. FIG. 11B. Without intending to be bound by any theory, these mRNA data suggest that the triple combination of EX M3, IDOi, and anti-PD-1 antibody resulted in both a substantial increase in CD8 T cells and reduced levels of the immunosuppressive Tregs, and that these changes in the T cell populations within the 4T1 tumor microenvironment likely contributed to the observed tumor regression.

What is claimed is:

1. A nucleic acid inhibitor molecule comprising a sense strand and an antisense strand and a region of complementarity between the sense strand and the antisense strand of 26 nucleotides,
wherein the sense strand comprises the nucleic acid of SEQ ID NO: 11;
wherein the antisense strand comprises the nucleic acid of SEQ ID NO: 12 and includes 2 single-stranded nucleotides at its 3' terminus and 10 single-stranded nucleotides at its 5' terminus.

2. The nucleic acid inhibitor molecule of claim 1, wherein the sense strand consists of the nucleic acid of SEQ ID NO: 11.

3. The nucleic acid inhibitor molecule of claim 1, wherein the antisense strand consists of the nucleic acid of SEQ ID NO: 12.

4. The nucleic acid inhibitor molecule of claim 1, wherein the sense strand consists of the nucleic acid of SEQ ID NO: 11 and the anti sense strand consists of the nucleic acid of SEQ ID NO: 12.

5. The nucleic acid inhibitor molecule of claim 1, wherein other than the 2'-F and 2'-OCH$_3$ modifications in SEQ ID NO: 11 and SEQ ID NO: 12, the nucleic acid inhibitor molecule does not contain any additional modifications.

6. The nucleic acid inhibitor molecule of claim 1, further comprising a 5'-phosphate mimic at the 5' terminus of the sense strand and/or the antisense strand.

7. The nucleic acid inhibitor molecule of claim 1, wherein the modified β-catenin nucleic acid inhibitor molecule is formulated with a nanoparticle.

8. The nucleic acid inhibitor molecule of claim 7, wherein the lipid nanoparticle comprises core lipids and envelope lipids, wherein the core lipids comprise a first cationic lipid and a first pegylated lipid and wherein the envelope lipids comprise a second cationic lipid, a neutral lipid, a sterol, and a second pegylated lipid.

9. The nucleic acid inhibitor molecule of claim 8, wherein the first cationic lipid is DL-048, the first pegylated lipid is DSG-MPEG, the second cationic lipid is DL-103, the neutral lipid is DSPC, the sterol is cholesterol, and the second pegylated lipid is DSPE-MPEG.

10. A pharmaceutical composition comprising a therapeutically effective amount of the nucleic acid inhibitor molecule of claim 1 and a pharmaceutically acceptable excipient.

11. A method for reducing expression of a β-catenin gene in a subject comprising administering the nucleic acid inhibitor molecule or pharmaceutical composition of claim 1 to a subject in need thereof in an amount sufficient to reduce expression of the β-catenin gene.

12. The method of claim 11, wherein the administering comprises intravenous, intramuscular, or subcutaneous administration.

13. The method of claim 11, wherein the subject is a human.

14. A method of treating a β-catenin-associated disorder in a subject, comprising administering to the subject a therapeutically effective amount of the nucleic acid inhibitor molecule or the pharmaceutical composition of claim 1, wherein the β-catenin-associated disorder is cancer.

15. The method of claim 14, wherein the administering comprises intravenous, intramuscular, or subcutaneous administration.

16. The method of claim 14, wherein the subject is a human.

17. The method of claim 14, wherein the cancer is colorectal cancer, hepatocellular carcinoma, or melanoma.

18. A pharmaceutical composition comprising the nucleic acid inhibitor molecule of claim 1 for use in treating a β-catenin-associated cancer.

* * * * *

```
                        SEQUENCE LISTING

<160> NUMBER OF SEQ ID NOS: 14

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: RNA base
<220> FEATURE:
<221> NAME/KEY: modified_base
<222> LOCATION: (2)..(2)
<223> OTHER INFORMATION: 2'Ome modified base
<220> FEATURE:
<221> NAME/KEY: modified_base
<222> LOCATION: (3)..(3)
<223> OTHER INFORMATION: RNA base
<220> FEATURE:
<221> NAME/KEY: modified_base
<222> LOCATION: (4)..(6)
<223> OTHER INFORMATION: 2'Ome modified base
<220> FEATURE:
<221> NAME/KEY: modified_base
<222> LOCATION: (7)..(7)
<223> OTHER INFORMATION: RNA base
<220> FEATURE:
<221> NAME/KEY: modified_base
<222> LOCATION: (8)..(8)
<223> OTHER INFORMATION: 2'Ome modified base
<220> FEATURE:
<221> NAME/KEY: modified_base
<222> LOCATION: (9)..(11)
<223> OTHER INFORMATION: RNA base
<220> FEATURE:
<221> NAME/KEY: modified_base
<222> LOCATION: (12)..(12)
<223> OTHER INFORMATION: 2'Ome modified base
<220> FEATURE:
<221> NAME/KEY: modified_base
<222> LOCATION: (13)..(13)
<223> OTHER INFORMATION: RNA base
<220> FEATURE:
<221> NAME/KEY: modified_base
<222> LOCATION: (14)..(14)
<223> OTHER INFORMATION: 2'Ome modified base
<220> FEATURE:
<221> NAME/KEY: modified_base
<222> LOCATION: (15)..(15)
<223> OTHER INFORMATION: RNA base
<220> FEATURE:
<221> NAME/KEY: modified_base
<222> LOCATION: (16)..(18)
<223> OTHER INFORMATION: 2'Ome modified base
<220> FEATURE:
<221> NAME/KEY: modified_base
<222> LOCATION: (19)..(23)
<223> OTHER INFORMATION: RNA base
<220> FEATURE:
<221> NAME/KEY: modified_base
<222> LOCATION: (24)..(25)
<223> OTHER INFORMATION: DNA base

<400> SEQUENCE: 1
agaauacaaa ugauguagaa acagc                                    25
```

```
<210> SEQ ID NO 2
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(4)
<223> OTHER INFORMATION: 2'Ome modified base
<220> FEATURE:
<221> NAME/KEY: modified_base
<222> LOCATION: (5)..(8)
<223> OTHER INFORMATION: RNA base
<220> FEATURE:
<221> NAME/KEY: modified_base
<222> LOCATION: (9)..(9)
<223> OTHER INFORMATION: 2'Ome modified base
<220> FEATURE:
<221> NAME/KEY: modified_base
<222> LOCATION: (10)..(10)
<223> OTHER INFORMATION: RNA base
<220> FEATURE:
<221> NAME/KEY: modified_base
<222> LOCATION: (11)..(11)
<223> OTHER INFORMATION: 2'Ome modified base
<220> FEATURE:
<221> NAME/KEY: modified_base
<222> LOCATION: (12)..(12)
<223> OTHER INFORMATION: RNA base
<220> FEATURE:
<221> NAME/KEY: modified_base
<222> LOCATION: (13)..(13)
<223> OTHER INFORMATION: 2'Ome modified base
<220> FEATURE:
<221> NAME/KEY: modified_base
<222> LOCATION: (14)..(14)
<223> OTHER INFORMATION: RNA base
<220> FEATURE:
<221> NAME/KEY: modified_base
<222> LOCATION: (15)..(15)
<223> OTHER INFORMATION: 2'Ome modified base
<220> FEATURE:
<221> NAME/KEY: modified_base
<222> LOCATION: (16)..(20)
<223> OTHER INFORMATION: RNA base
<220> FEATURE:
<221> NAME/KEY: modified_base
<222> LOCATION: (21)..(21)
<223> OTHER INFORMATION: 2'Ome modified base
<220> FEATURE:
<221> NAME/KEY: modified_base
<222> LOCATION: (22)..(22)
<223> OTHER INFORMATION: RNA base
<220> FEATURE:
<221> NAME/KEY: modified_base
<222> LOCATION: (23)..(23)
<223> OTHER INFORMATION: 2'Ome modified base
<220> FEATURE:
<221> NAME/KEY: modified_base
<222> LOCATION: (24)..(24)
<223> OTHER INFORMATION: RNA base
<220> FEATURE:
<221> NAME/KEY: modified_base
<222> LOCATION: (25)..(27)
<223> OTHER INFORMATION: 2'Ome modified base

<400> SEQUENCE: 2
gcuguuucua caucauuugu auucugc                                        27

<210> SEQ ID NO 3
<211> LENGTH: 25
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: 2'F modified base
<220> FEATURE:
<221> NAME/KEY: modified_base
<222> LOCATION: (2)..(2)
<223> OTHER INFORMATION: 2'Ome modified base
<220> FEATURE:
<221> NAME/KEY: modified_base
<222> LOCATION: (3)..(3)
<223> OTHER INFORMATION: 2'F modified base
<220> FEATURE:
<221> NAME/KEY: modified_base
<222> LOCATION: (4)..(6)
<223> OTHER INFORMATION: 2'Ome modified base
<220> FEATURE:
<221> NAME/KEY: modified_base
<222> LOCATION: (7)..(7)
<223> OTHER INFORMATION: 2'F modified base
<220> FEATURE:
<221> NAME/KEY: modified_base
<222> LOCATION: (8)..(8)
<223> OTHER INFORMATION: 2'Ome modified base
<220> FEATURE:
<221> NAME/KEY: modified_base
<222> LOCATION: (9)..(11)
<223> OTHER INFORMATION: 2'F modified base
<220> FEATURE:
<221> NAME/KEY: modified_base
<222> LOCATION: (12)..(12)
<223> OTHER INFORMATION: 2'Ome modified base
<220> FEATURE:
<221> NAME/KEY: modified_base
<222> LOCATION: (13)..(13)
<223> OTHER INFORMATION: 2'F modified base
<220> FEATURE:
<221> NAME/KEY: modified_base
<222> LOCATION: (14)..(14)
<223> OTHER INFORMATION: 2'Ome modified base
<220> FEATURE:
<221> NAME/KEY: modified_base
<222> LOCATION: (15)..(15)
<223> OTHER INFORMATION: 2'F modified base
<220> FEATURE:
<221> NAME/KEY: modified_base
<222> LOCATION: (16)..(18)
<223> OTHER INFORMATION: 2'Ome modified base
<220> FEATURE:
<221> NAME/KEY: modified_base
<222> LOCATION: (19)..(23)
<223> OTHER INFORMATION: RNA base
<220> FEATURE:
<221> NAME/KEY: modified_base
<222> LOCATION: (24)..(25)
<223> OTHER INFORMATION: DNA base

<400> SEQUENCE: 3
agaauacaaa ugauguagaa acagc                                           25

<210> SEQ ID NO 4
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(4)
<223> OTHER INFORMATION: 2'Ome modified base
<220> FEATURE:
```

```
<221> NAME/KEY: modified_base
<222> LOCATION: (5)..(7)
<223> OTHER INFORMATION: RNA base
<220> FEATURE:
<221> NAME/KEY: modified_base
<222> LOCATION: (8)..(8)
<223> OTHER INFORMATION: 2'F modified base
<220> FEATURE:
<221> NAME/KEY: modified_base
<222> LOCATION: (9)..(9)
<223> OTHER INFORMATION: 2'Ome modified base
<220> FEATURE:
<221> NAME/KEY: modified_base
<222> LOCATION: (10)..(10)
<223> OTHER INFORMATION: 2'F modified base
<220> FEATURE:
<221> NAME/KEY: modified_base
<222> LOCATION: (11)..(11)
<223> OTHER INFORMATION: 2'Ome modified base
<220> FEATURE:
<221> NAME/KEY: modified_base
<222> LOCATION: (12)..(12)
<223> OTHER INFORMATION: 2'F modified base
<220> FEATURE:
<221> NAME/KEY: modified_base
<222> LOCATION: (13)..(13)
<223> OTHER INFORMATION: 2'Ome modified base
<220> FEATURE:
<221> NAME/KEY: modified_base
<222> LOCATION: (14)..(14)
<223> OTHER INFORMATION: 2'F modified base
<220> FEATURE:
<221> NAME/KEY: modified_base
<222> LOCATION: (15)..(15)
<223> OTHER INFORMATION: 2'Ome modified base
<220> FEATURE:
<221> NAME/KEY: modified_base
<222> LOCATION: (16)..(19)
<223> OTHER INFORMATION: RNA base
<220> FEATURE:
<221> NAME/KEY: modified_base
<222> LOCATION: (20)..(20)
<223> OTHER INFORMATION: 2'F modified base
<220> FEATURE:
<221> NAME/KEY: modified_base
<222> LOCATION: (21)..(21)
<223> OTHER INFORMATION: 2'Ome modified base
<220> FEATURE:
<221> NAME/KEY: modified_base
<222> LOCATION: (22)..(22)
<223> OTHER INFORMATION: 2'F modified base
<220> FEATURE:
<221> NAME/KEY: modified_base
<222> LOCATION: (23)..(23)
<223> OTHER INFORMATION: 2'Ome modified base
<220> FEATURE:
<221> NAME/KEY: modified_base
<222> LOCATION: (24)..(24)
<223> OTHER INFORMATION: 2'F modified base
<220> FEATURE:
<221> NAME/KEY: modified_base
<222> LOCATION: (25)..(27)
<223> OTHER INFORMATION: 2'Ome modified base

<400> SEQUENCE: 4
gcuguuucua caucauuugu auucugc                                             27

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

```
<220> FEATURE:
<221> NAME/KEY: modified_base
<222> LOCATION: (1)..(1)
<223> OTHER INFORMATION: 2'F modified base
<220> FEATURE:
<221> NAME/KEY: modified_base
<222> LOCATION: (2)..(2)
<223> OTHER INFORMATION: 2'Ome modified base
<220> FEATURE:
<221> NAME/KEY: modified_base
<222> LOCATION: (3)..(3)
<223> OTHER INFORMATION: 2'F modified base
<220> FEATURE:
<221> NAME/KEY: modified_base
<222> LOCATION: (4)..(6)
<223> OTHER INFORMATION: 2'Ome modified base
<220> FEATURE:
<221> NAME/KEY: modified_base
<222> LOCATION: (7)..(7)
<223> OTHER INFORMATION: 2'F modified base
<220> FEATURE:
<221> NAME/KEY: modified_base
<222> LOCATION: (8)..(8)
<223> OTHER INFORMATION: 2'Ome modified base
<220> FEATURE:
<221> NAME/KEY: modified_base
<222> LOCATION: (9)..(11)
<223> OTHER INFORMATION: 2'F modified base
<220> FEATURE:
<221> NAME/KEY: modified_base
<222> LOCATION: (12)..(12)
<223> OTHER INFORMATION: 2'Ome modified base
<220> FEATURE:
<221> NAME/KEY: modified_base
<222> LOCATION: (13)..(13)
<223> OTHER INFORMATION: 2'F modified base
<220> FEATURE:
<221> NAME/KEY: modified_base
<222> LOCATION: (14)..(14)
<223> OTHER INFORMATION: 2'Ome modified base
<220> FEATURE:
<221> NAME/KEY: modified_base
<222> LOCATION: (15)..(15)
<223> OTHER INFORMATION: 2'F modified base
<220> FEATURE:
<221> NAME/KEY: modified_base
<222> LOCATION: (16)..(18)
<223> OTHER INFORMATION: 2'Ome modified base
<220> FEATURE:
<221> NAME/KEY: modified_base
<222> LOCATION: (19)..(21)
<223> OTHER INFORMATION: 2'F modified base
<220> FEATURE:
<221> NAME/KEY: modified_base
<222> LOCATION: (22)..(23)
<223> OTHER INFORMATION: RNA base
<220> FEATURE:
<221> NAME/KEY: modified_base
<222> LOCATION: (24)..(25)
<223> OTHER INFORMATION: DNA base

<400> SEQUENCE: 5
agaauacaaa ugauguagaa acagc                                         25

<210> SEQ ID NO 6
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(4)
<223> OTHER INFORMATION: 2'Ome modified base
<220> FEATURE:
<221> NAME/KEY: modified_base
```

<222> LOCATION: (5)..(7)
<223> OTHER INFORMATION: RNA base
<220> FEATURE:
<221> NAME/KEY: modified_base
<222> LOCATION: (8)..(8)
<223> OTHER INFORMATION: 2'F modified base
<220> FEATURE:
<221> NAME/KEY: modified_base
<222> LOCATION: (9)..(9)
<223> OTHER INFORMATION: 2'Ome modified base
<220> FEATURE:
<221> NAME/KEY: modified_base
<222> LOCATION: (10)..(10)
<223> OTHER INFORMATION: 2'F modified base
<220> FEATURE:
<221> NAME/KEY: modified_base
<222> LOCATION: (11)..(11)
<223> OTHER INFORMATION: 2'Ome modified base
<220> FEATURE:
<221> NAME/KEY: modified_base
<222> LOCATION: (12)..(12)
<223> OTHER INFORMATION: 2'F modified base
<220> FEATURE:
<221> NAME/KEY: modified_base
<222> LOCATION: (13)..(13)
<223> OTHER INFORMATION: 2'Ome modified base
<220> FEATURE:
<221> NAME/KEY: modified_base
<222> LOCATION: (14)..(14)
<223> OTHER INFORMATION: 2'F modified base
<220> FEATURE:
<221> NAME/KEY: modified_base
<222> LOCATION: (15)..(15)
<223> OTHER INFORMATION: 2'Ome modified base
<220> FEATURE:
<221> NAME/KEY: modified_base
<222> LOCATION: (16)..(18)
<223> OTHER INFORMATION: RNA base
<220> FEATURE:
<221> NAME/KEY: modified_base
<222> LOCATION: (19)..(20)
<223> OTHER INFORMATION: 2'F modified base
<220> FEATURE:
<221> NAME/KEY: modified_base
<222> LOCATION: (21)..(21)
<223> OTHER INFORMATION: 2'Ome modified base
<220> FEATURE:
<221> NAME/KEY: modified_base
<222> LOCATION: (22)..(22)
<223> OTHER INFORMATION: 2'F modified base
<220> FEATURE:
<221> NAME/KEY: modified_base
<222> LOCATION: (23)..(23)
<223> OTHER INFORMATION: 2'Ome modified base
<220> FEATURE:
<221> NAME/KEY: modified_base
<222> LOCATION: (24)..(24)
<223> OTHER INFORMATION: 2'F modified base
<220> FEATURE:
<221> NAME/KEY: modified_base
<222> LOCATION: (25)..(27)
<223> OTHER INFORMATION: 2'Ome modified base

<400> SEQUENCE: 6
gcuguuucua caucauuugu auucugc                                27

<210> SEQ ID NO 7
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:

-continued

```
<221> NAME/KEY: modified_base
<222> LOCATION: (1)..(1)
<223> OTHER INFORMATION: RNA base
<220> FEATURE:
<221> NAME/KEY: modified_base
<222> LOCATION: (2)..(2)
<223> OTHER INFORMATION: 2'Ome modified base
<220> FEATURE:
<221> NAME/KEY: modified_base
<222> LOCATION: (3)..(3)
<223> OTHER INFORMATION: RNA base
<220> FEATURE:
<221> NAME/KEY: modified_base
<222> LOCATION: (4)..(6)
<223> OTHER INFORMATION: 2'Ome modified base
<220> FEATURE:
<221> NAME/KEY: modified_base
<222> LOCATION: (7)..(7)
<223> OTHER INFORMATION: RNA base
<220> FEATURE:
<221> NAME/KEY: modified_base
<222> LOCATION: (8)..(8)
<223> OTHER INFORMATION: 2'Ome modified base
<220> FEATURE:
<221> NAME/KEY: modified_base
<222> LOCATION: (9)..(11)
<223> OTHER INFORMATION: RNA base
<220> FEATURE:
<221> NAME/KEY: modified_base
<222> LOCATION: (12)..(12)
<223> OTHER INFORMATION: 2'Ome modified base
<220> FEATURE:
<221> NAME/KEY: modified_base
<222> LOCATION: (13)..(13)
<223> OTHER INFORMATION: RNA base
<220> FEATURE:
<221> NAME/KEY: modified_base
<222> LOCATION: (14)..(14)
<223> OTHER INFORMATION: 2'Ome modified base
<220> FEATURE:
<221> NAME/KEY: modified_base
<222> LOCATION: (15)..(15)
<223> OTHER INFORMATION: RNA base
<220> FEATURE:
<221> NAME/KEY: modified_base
<222> LOCATION: (16)..(18)
<223> OTHER INFORMATION: 2'Ome modified base
<220> FEATURE:
<221> NAME/KEY: modified_base
<222> LOCATION: (19)..(23)
<223> OTHER INFORMATION: RNA base
<220> FEATURE:
<221> NAME/KEY: modified_base
<222> LOCATION: (24)..(24)
<223> OTHER INFORMATION: 2'Ome modified base
<220> FEATURE:
<221> NAME/KEY: modified_base
<222> LOCATION: (25)..(26)
<223> OTHER INFORMATION: DNA base

<400> SEQUENCE: 7
agaauacaaa ugauguagaa acagcc                                        26

<210> SEQ ID NO 8
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: 2'Ome modified base
```

```
<220> FEATURE:
<221> NAME/KEY: modified_base
<222> LOCATION: (2)..(2)
<223> OTHER INFORMATION: 2'F modified base
<220> FEATURE:
<221> NAME/KEY: modified_base
<222> LOCATION: (3)..(5)
<223> OTHER INFORMATION: 2'Ome modified base
<220> FEATURE:
<221> NAME/KEY: modified_base
<222> LOCATION: (6)..(6)
<223> OTHER INFORMATION: 2'F modified base
<220> FEATURE:
<221> NAME/KEY: modified_base
<222> LOCATION: (7)..(9)
<223> OTHER INFORMATION: 2'Ome modified base
<220> FEATURE:
<221> NAME/KEY: modified_base
<222> LOCATION: (10)..(10)
<223> OTHER INFORMATION: DNA base
<220> FEATURE:
<221> NAME/KEY: modified_base
<222> LOCATION: (11)..(15)
<223> OTHER INFORMATION: 2'Ome modified base
<220> FEATURE:
<221> NAME/KEY: modified_base
<222> LOCATION: (16)..(19)
<223> OTHER INFORMATION: RNA base
<220> FEATURE:
<221> NAME/KEY: modified_base
<222> LOCATION: (20)..(20)
<223> OTHER INFORMATION: 2'Ome modified base
<220> FEATURE:
<221> NAME/KEY: modified_base
<222> LOCATION: (21)..(21)
<223> OTHER INFORMATION: RNA base
<220> FEATURE:
<221> NAME/KEY: modified_base
<222> LOCATION: (22)..(22)
<223> OTHER INFORMATION: 2'Ome modified base
<220> FEATURE:
<221> NAME/KEY: modified_base
<222> LOCATION: (23)..(23)
<223> OTHER INFORMATION: RNA base
<220> FEATURE:
<221> NAME/KEY: modified_base
<222> LOCATION: (24)..(24)
<223> OTHER INFORMATION: 2'Ome modified base
<220> FEATURE:
<221> NAME/KEY: modified_base
<222> LOCATION: (25)..(25)
<223> OTHER INFORMATION: RNA base
<220> FEATURE:
<221> NAME/KEY: modified_base
<222> LOCATION: (26)..(26)
<223> OTHER INFORMATION: 2'Ome modified base
<220> FEATURE:
<221> NAME/KEY: modified_base
<222> LOCATION: (27)..(31)
<223> OTHER INFORMATION: RNA base
<220> FEATURE:
<221> NAME/KEY: modified_base
<222> LOCATION: (32)..(32)
<223> OTHER INFORMATION: 2'Ome modified base
<220> FEATURE:
<221> NAME/KEY: modified_base
<222> LOCATION: (33)..(33)
<223> OTHER INFORMATION: RNA base
<220> FEATURE:
<221> NAME/KEY: modified_base
<222> LOCATION: (34)..(34)
<223> OTHER INFORMATION: 2'Ome modified base
<220> FEATURE:
<221> NAME/KEY: modified_base
<222> LOCATION: (35)..(35)
<223> OTHER INFORMATION: RNA base
<220> FEATURE:
<221> NAME/KEY: modified_base
<222> LOCATION: (36)..(38)
```

<223> OTHER INFORMATION: 2'Ome modified base

<400> SEQUENCE: 8
uagcuaucgt ggcuguuucu acaucauuug uauucugc                               38

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: 2'F modified base
<220> FEATURE:
<221> NAME/KEY: modified_base
<222> LOCATION: (2)..(2)
<223> OTHER INFORMATION: 2'Ome modified base
<220> FEATURE:
<221> NAME/KEY: modified_base
<222> LOCATION: (3)..(3)
<223> OTHER INFORMATION: 2'F modified base
<220> FEATURE:
<221> NAME/KEY: modified_base
<222> LOCATION: (4)..(6)
<223> OTHER INFORMATION: 2'Ome modified base
<220> FEATURE:
<221> NAME/KEY: modified_base
<222> LOCATION: (7)..(7)
<223> OTHER INFORMATION: 2'F modified base
<220> FEATURE:
<221> NAME/KEY: modified_base
<222> LOCATION: (8)..(8)
<223> OTHER INFORMATION: 2'Ome modified base
<220> FEATURE:
<221> NAME/KEY: modified_base
<222> LOCATION: (9)..(11)
<223> OTHER INFORMATION: 2'F modified base
<220> FEATURE:
<221> NAME/KEY: modified_base
<222> LOCATION: (12)..(12)
<223> OTHER INFORMATION: 2'Ome modified base
<220> FEATURE:
<221> NAME/KEY: modified_base
<222> LOCATION: (13)..(13)
<223> OTHER INFORMATION: 2'F modified base
<220> FEATURE:
<221> NAME/KEY: modified_base
<222> LOCATION: (14)..(14)
<223> OTHER INFORMATION: 2'Ome modified base
<220> FEATURE:
<221> NAME/KEY: modified_base
<222> LOCATION: (15)..(15)
<223> OTHER INFORMATION: 2'F modified base
<220> FEATURE:
<221> NAME/KEY: modified_base
<222> LOCATION: (16)..(18)
<223> OTHER INFORMATION: 2'Ome modified base
<220> FEATURE:
<221> NAME/KEY: modified_base
<222> LOCATION: (19)..(23)
<223> OTHER INFORMATION: RNA base
<220> FEATURE:
<221> NAME/KEY: modified_base
<222> LOCATION: (24)..(24)
<223> OTHER INFORMATION: 2'Ome modified base
<220> FEATURE:
<221> NAME/KEY: modified_base
<222> LOCATION: (25)..(26)
<223> OTHER INFORMATION: DNA base

<400> SEQUENCE: 9
agaauacaaa ugauguagaa acagcc                                           26

<210> SEQ ID NO 10
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: 2'Ome modified base
<220> FEATURE:
<221> NAME/KEY: modified_base
<222> LOCATION: (2)..(2)
<223> OTHER INFORMATION: 2'F modified base
<220> FEATURE:
<221> NAME/KEY: modified_base
<222> LOCATION: (3)..(5)
<223> OTHER INFORMATION: 2'Ome modified base
<220> FEATURE:
<221> NAME/KEY: modified_base
<222> LOCATION: (6)..(6)
<223> OTHER INFORMATION: 2'F modified base
<220> FEATURE:
<221> NAME/KEY: modified_base
<222> LOCATION: (7)..(9)
<223> OTHER INFORMATION: 2'Ome modified base
<220> FEATURE:
<221> NAME/KEY: modified_base
<222> LOCATION: (10)..(10)
<223> OTHER INFORMATION: DNA base
<220> FEATURE:
<221> NAME/KEY: modified_base
<222> LOCATION: (11)..(15)
<223> OTHER INFORMATION: 2'Ome modified base
<220> FEATURE:
<221> NAME/KEY: modified_base
<222> LOCATION: (16)..(18)
<223> OTHER INFORMATION: RNA base
<220> FEATURE:
<221> NAME/KEY: modified_base
<222> LOCATION: (19)..(19)
<223> OTHER INFORMATION: 2'F modified base
<220> FEATURE:
<221> NAME/KEY: modified_base
<222> LOCATION: (20)..(20)
<223> OTHER INFORMATION: 2'Ome modified base
<220> FEATURE:
<221> NAME/KEY: modified_base
<222> LOCATION: (21)..(21)
<223> OTHER INFORMATION: 2'F modified base
<220> FEATURE:
<221> NAME/KEY: modified_base
<222> LOCATION: (22)..(22)
<223> OTHER INFORMATION: 2'Ome modified base
<220> FEATURE:
<221> NAME/KEY: modified_base
<222> LOCATION: (23)..(23)
<223> OTHER INFORMATION: 2'F modified base
<220> FEATURE:
<221> NAME/KEY: modified_base
<222> LOCATION: (24)..(24)
<223> OTHER INFORMATION: 2'Ome modified base
<220> FEATURE:
<221> NAME/KEY: modified_base
<222> LOCATION: (25)..(25)
<223> OTHER INFORMATION: 2'F modified base
<220> FEATURE:
<221> NAME/KEY: modified_base
<222> LOCATION: (26)..(26)
<223> OTHER INFORMATION: 2'Ome modified base
<220> FEATURE:

<220> FEATURE:
<221> NAME/KEY: modified_base
<222> LOCATION: (27)..(30)
<223> OTHER INFORMATION: RNA base
<220> FEATURE:
<221> NAME/KEY: modified_base
<222> LOCATION: (31)..(31)
<223> OTHER INFORMATION: 2'F modified base
<220> FEATURE:
<221> NAME/KEY: modified_base
<222> LOCATION: (32)..(32)
<223> OTHER INFORMATION: 2'Ome modified base
<220> FEATURE:
<221> NAME/KEY: modified_base
<222> LOCATION: (33)..(33)
<223> OTHER INFORMATION: 2'F modified base
<220> FEATURE:
<221> NAME/KEY: modified_base
<222> LOCATION: (34)..(34)
<223> OTHER INFORMATION: 2'Ome modified base
<220> FEATURE:
<221> NAME/KEY: modified_base
<222> LOCATION: (35)..(35)
<223> OTHER INFORMATION: 2'F modified base
<220> FEATURE:
<221> NAME/KEY: modified_base
<222> LOCATION: (36)..(38)
<223> OTHER INFORMATION: 2'Ome modified base

<400> SEQUENCE: 10
uagcuaucgt ggcuguuucu acaucauuug uauucugc         38

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: 2'F modified base
<220> FEATURE:
<221> NAME/KEY: modified_base
<222> LOCATION: (2)..(2)
<223> OTHER INFORMATION: 2'Ome modified base
<220> FEATURE:
<221> NAME/KEY: modified_base
<222> LOCATION: (3)..(3)
<223> OTHER INFORMATION: 2'F modified base
<220> FEATURE:
<221> NAME/KEY: modified_base
<222> LOCATION: (4)..(6)
<223> OTHER INFORMATION: 2'Ome modified base
<220> FEATURE:
<221> NAME/KEY: modified_base
<222> LOCATION: (7)..(7)
<223> OTHER INFORMATION: 2'F modified base
<220> FEATURE:
<221> NAME/KEY: modified_base
<222> LOCATION: (8)..(8)
<223> OTHER INFORMATION: 2'Ome modified base
<220> FEATURE:
<221> NAME/KEY: modified_base
<222> LOCATION: (9)..(11)
<223> OTHER INFORMATION: 2'F modified base
<220> FEATURE:
<221> NAME/KEY: modified_base
<222> LOCATION: (12)..(12)
<223> OTHER INFORMATION: 2'Ome modified base
<220> FEATURE:
<221> NAME/KEY: modified_base
<222> LOCATION: (13)..(13)
<223> OTHER INFORMATION: 2'F modified base -continued

```
<220> FEATURE:
<221> NAME/KEY: modified_base
<222> LOCATION: (14)..(14)
<223> OTHER INFORMATION: 2'Ome modified base
<220> FEATURE:
<221> NAME/KEY: modified_base
<222> LOCATION: (15)..(15)
<223> OTHER INFORMATION: 2'F modified base
<220> FEATURE:
<221> NAME/KEY: modified_base
<222> LOCATION: (16)..(18)
<223> OTHER INFORMATION: 2'Ome modified base
<220> FEATURE:
<221> NAME/KEY: modified_base
<222> LOCATION: (19)..(20)
<223> OTHER INFORMATION: 2'F modified base
<220> FEATURE:
<221> NAME/KEY: modified_base
<222> LOCATION: (21)..(23)
<223> OTHER INFORMATION: RNA base
<220> FEATURE:
<221> NAME/KEY: modified_base
<222> LOCATION: (24)..(24)
<223> OTHER INFORMATION: 2'Ome modified base
<220> FEATURE:
<221> NAME/KEY: modified_base
<222> LOCATION: (25)..(26)
<223> OTHER INFORMATION: DNA base

<400> SEQUENCE: 11
agaauacaaa ugauguagaa acagcc                                          26

<210> SEQ ID NO 12
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: 2'Ome modified base
<220> FEATURE:
<221> NAME/KEY: modified_base
<222> LOCATION: (2)..(2)
<223> OTHER INFORMATION: 2'F modified base
<220> FEATURE:
<221> NAME/KEY: modified_base
<222> LOCATION: (3)..(5)
<223> OTHER INFORMATION: 2'Ome modified base
<220> FEATURE:
<221> NAME/KEY: modified_base
<222> LOCATION: (6)..(6)
<223> OTHER INFORMATION: 2'F modified base
<220> FEATURE:
<221> NAME/KEY: modified_base
<222> LOCATION: (7)..(9)
<223> OTHER INFORMATION: 2'Ome modified base
<220> FEATURE:
<221> NAME/KEY: modified_base
<222> LOCATION: (10)..(10)
<223> OTHER INFORMATION: DNA base
<220> FEATURE:
<221> NAME/KEY: modified_base
<222> LOCATION: (11)..(15)
<223> OTHER INFORMATION: 2'Ome modified base
<220> FEATURE:
<221> NAME/KEY: modified_base
<222> LOCATION: (16)..(18)
<223> OTHER INFORMATION: RNA base
<220> FEATURE:
<221> NAME/KEY: modified_base
<222> LOCATION: (19)..(19)
```

```
<223> OTHER INFORMATION: 2'F modified base
<220> FEATURE:
<221> NAME/KEY: modified_base
<222> LOCATION: (20)..(20)
<223> OTHER INFORMATION: 2'Ome modified base
<220> FEATURE:
<221> NAME/KEY: modified_base
<222> LOCATION: (21)..(21)
<223> OTHER INFORMATION: 2'F modified base
<220> FEATURE:
<221> NAME/KEY: modified_base
<222> LOCATION: (22)..(22)
<223> OTHER INFORMATION: 2'Ome modified base
<220> FEATURE:
<221> NAME/KEY: modified_base
<222> LOCATION: (23)..(23)
<223> OTHER INFORMATION: 2'F modified base
<220> FEATURE:
<221> NAME/KEY: modified_base
<222> LOCATION: (24)..(24)
<223> OTHER INFORMATION: 2'Ome modified base
<220> FEATURE:
<221> NAME/KEY: modified_base
<222> LOCATION: (25)..(25)
<223> OTHER INFORMATION: 2'F modified base
<220> FEATURE:
<221> NAME/KEY: modified_base
<222> LOCATION: (26)..(26)
<223> OTHER INFORMATION: 2'Ome modified base
<220> FEATURE:
<221> NAME/KEY: modified_base
<222> LOCATION: (27)..(29)
<223> OTHER INFORMATION: RNA base
<220> FEATURE:
<221> NAME/KEY: modified_base
<222> LOCATION: (30)..(31)
<223> OTHER INFORMATION: 2'F modified base
<220> FEATURE:
<221> NAME/KEY: modified_base
<222> LOCATION: (32)..(32)
<223> OTHER INFORMATION: 2'Ome modified base
<220> FEATURE:
<221> NAME/KEY: modified_base
<222> LOCATION: (33)..(33)
<223> OTHER INFORMATION: 2'F modified base
<220> FEATURE:
<221> NAME/KEY: modified_base
<222> LOCATION: (34)..(34)
<223> OTHER INFORMATION: 2'Ome modified base
<220> FEATURE:
<221> NAME/KEY: modified_base
<222> LOCATION: (35)..(35)
<223> OTHER INFORMATION: 2'F modified base
<220> FEATURE:
<221> NAME/KEY: modified_base
<222> LOCATION: (36)..(38)
<223> OTHER INFORMATION: 2'Ome modified base

<400> SEQUENCE: 12
uagcuaucgt ggcuguuucu acaucauuug uauucugc                              38

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 13
agaauacaaa ugauguagaa acagcc                                          26
```

```
<210> SEQ ID NO 14
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 14
uagcuaucgt ggcuguuucu acaucauuug uauucugc                              38
```